(12) United States Patent
Podhajsky et al.

(10) Patent No.: US 9,377,367 B2
(45) Date of Patent: Jun. 28, 2016

(54) SPECIFIC ABSORPTION RATE MEASUREMENT AND ENERGY-DELIVERY DEVICE CHARACTERIZATION USING THERMAL PHANTOM AND IMAGE ANALYSIS

(75) Inventors: Ronald J. Podhajsky, Boulder, CO (US); Jonathan A. Coe, Denver, CO (US)

(73) Assignee: Covidien LP, Mansfield, MA (US)

( * ) Notice: Subject to any disclaimer, the term of this patent is extended or adjusted under 35 U.S.C. 154(b) by 634 days.

(21) Appl. No.: 12/792,970

(22) Filed: Jun. 3, 2010

(65) Prior Publication Data
US 2011/0299719 A1    Dec. 8, 2011

(51) Int. Cl.
| G06K 9/00 | (2006.01) |
| G06G 7/48 | (2006.01) |
| G01K 11/12 | (2006.01) |
| A61B 18/18 | (2006.01) |

(52) U.S. Cl.
CPC ............ *G01K 11/12* (2013.01); *A61B 18/1815* (2013.01)

(58) Field of Classification Search
CPC ............... A61B 18/1815; A61B 18/18; A61B 18/1477; A61B 2018/00577; A61B 2018/00702; A61B 2018/00791; A61B 19/50; A61B 2018/00922; A61B 2018/00642; A61B 18/0016; A61B 2018/00648; A61B 2018/124; A61B 2018/143; A61B 2018/00714; A61B 2018/183; A61B 5/015; A61B 5/743; A61B 18/04; A61B 18/14; A61B 2018/0016
USPC .......................... 382/155; 250/339.04; 374/32
See application file for complete search history.

(56) References Cited

U.S. PATENT DOCUMENTS

| D263,020 | S |   | 2/1982  | Rau, III |
| 4,372,315 | A |   | 2/1983  | Shapiro et al. |
| 4,700,716 | A |   | 10/1987 | Kasevich et al. |
| D295,893 | S |   | 5/1988  | Sharkany et al. |
| D295,894 | S |   | 5/1988  | Sharkany et al. |
| 4,825,880 | A |   | 5/1989  | Stauffer et al. |
| 4,860,752 | A | * | 8/1989  | Turner ......................... 607/102 |
| 4,967,765 | A | * | 11/1990 | Turner et al. .................. 607/154 |
| 5,097,846 | A |   | 3/1992  | Larsen |
| 5,344,435 | A |   | 9/1994  | Turner et al. |
| 5,610,519 | A |   | 3/1997  | Hankui et al. |
| 5,683,382 | A |   | 11/1997 | Lenihan et al. |
| 5,789,929 | A |   | 8/1998  | Hankui |
| 5,904,709 | A |   | 5/1999  | Arndt et al. |
| D424,694 | S |   | 5/2000  | Tetzlaff et al. |
| D425,201 | S |   | 5/2000  | Tetzlaff et al. |

(Continued)

FOREIGN PATENT DOCUMENTS

| CN | 1103807 | 6/1995 |
| DE | 390937 | 3/1924 |

(Continued)

OTHER PUBLICATIONS

US 5,326,343, 7/1994, Rudie et al. (withdrawn).

(Continued)

*Primary Examiner* — Kim Vu
*Assistant Examiner* — Michael Vanchy, Jr.

(57) ABSTRACT

A method of predicting a radiation pattern emitted by an energy applicator includes the steps of providing thermal profile data for an energy applicator, determining a specific absorption rate around the energy applicator as a function of the thermal profile data, and generating a simulated radiation pattern for the energy applicator as a function of the determined specific absorption rate.

16 Claims, 17 Drawing Sheets

(56) References Cited

U.S. PATENT DOCUMENTS

| | | | |
|---|---|---|---|
| 6,080,149 A | 6/2000 | Huang et al. | |
| 6,163,726 A | 12/2000 | Wolf | |
| 6,181,136 B1 | 1/2001 | Choi et al. | |
| 6,241,725 B1 | 6/2001 | Cosman | |
| 6,277,113 B1 | 8/2001 | Berube | |
| D449,886 S | 10/2001 | Tetzlaff et al. | |
| 6,306,132 B1 | 10/2001 | Moorman et al. | |
| 6,355,033 B1 | 3/2002 | Moorman | |
| D457,958 S | 5/2002 | Dycus et al. | |
| D457,959 S | 5/2002 | Tetzlaff et al. | |
| 6,470,217 B1 | 10/2002 | Fenn et al. | |
| 6,477,426 B1 | 11/2002 | Fenn et al. | |
| 6,562,037 B2 | 5/2003 | Paton et al. | |
| 6,582,426 B2 | 6/2003 | Moorman | |
| 6,652,520 B2 | 11/2003 | Moorman | |
| D496,997 S | 10/2004 | Dycus et al. | |
| 6,807,446 B2 | 10/2004 | Fenn et al. | |
| D499,181 S | 11/2004 | Dycus et al. | |
| 6,919,845 B2 | 7/2005 | Ozaki et al. | |
| 7,001,383 B2 | 2/2006 | Keidar | |
| 7,025,765 B2 | 4/2006 | Balbierz et al. | |
| D525,361 S | 7/2006 | Hushka | |
| 7,089,064 B2 | 8/2006 | Manker et al. | |
| D531,311 S | 10/2006 | Guerra et al. | |
| D533,942 S | 12/2006 | Kerr et al. | |
| D535,027 S | 1/2007 | James et al. | |
| 7,160,292 B2 | 1/2007 | Moorman | |
| 7,180,307 B2 | 2/2007 | Wakino et al. | |
| D541,418 S | 4/2007 | Schechter et al. | |
| D541,938 S | 5/2007 | Kerr et al. | |
| 7,298,880 B2 | 11/2007 | Nishiura | |
| D564,662 S | 3/2008 | Moses et al. | |
| 7,344,533 B2 | 3/2008 | Pearson et al. | |
| 7,367,972 B2 | 5/2008 | Francishelli et al. | |
| 7,512,283 B2 | 3/2009 | Brower et al. | |
| 7,583,820 B2 | 9/2009 | Nishiura | |
| 7,587,065 B2 | 9/2009 | Matsumoto et al. | |
| D613,412 S | 4/2010 | DeCarlo | |
| 7,699,842 B2 | 4/2010 | Buysse et al. | |
| 7,702,495 B2 | 4/2010 | Humphries et al. | |
| 8,073,551 B2* | 12/2011 | McCann et al. | 607/101 |
| 8,319,495 B1* | 11/2012 | Zhu | 324/307 |
| 2006/0030914 A1 | 2/2006 | Eggers et al. | |
| 2006/0064002 A1* | 3/2006 | Grist et al. | 600/410 |
| 2006/0241523 A1* | 10/2006 | Sinelnikov et al. | 601/2 |
| 2006/0289528 A1 | 12/2006 | Chiu et al. | |
| 2007/0161977 A1 | 7/2007 | Moorman | |
| 2007/0233057 A1 | 10/2007 | Konishi | |
| 2007/0236229 A1 | 10/2007 | Onishi et al. | |
| 2008/0015664 A1* | 1/2008 | Podhajsky | 607/99 |
| 2008/0123716 A1 | 5/2008 | Podhajsky et al. | |
| 2008/0183165 A1 | 7/2008 | Buysse et al. | |
| 2009/0054887 A1 | 2/2009 | Podhajsky | |
| 2010/0049185 A1 | 2/2010 | Paulus | |
| 2010/0076422 A1 | 3/2010 | Podhajsky | |
| 2010/0087808 A1 | 4/2010 | Paulus | |
| 2010/0092939 A1 | 4/2010 | Belous et al. | |
| 2010/0094272 A1 | 4/2010 | Rossetto et al. | |
| 2010/0094273 A1 | 4/2010 | Rossetto et al. | |
| 2010/0179532 A1 | 7/2010 | Buysse et al. | |

FOREIGN PATENT DOCUMENTS

| | | |
|---|---|---|
| DE | 1099658 | 2/1961 |
| DE | 1139927 | 11/1962 |
| DE | 1149832 | 6/1963 |
| DE | 1439302 | 1/1969 |
| DE | 2439587 | 2/1975 |
| DE | 2455174 | 5/1975 |
| DE | 2407559 | 8/1975 |
| DE | 2415263 | 10/1975 |
| DE | 2429021 | 1/1976 |
| DE | 2460481 | 6/1976 |
| DE | 2602517 | 7/1976 |
| DE | 2504280 | 8/1976 |
| DE | 2627679 | 1/1977 |
| DE | 2540968 | 3/1977 |
| DE | 2820908 | 11/1978 |
| DE | 2803275 | 8/1979 |
| DE | 2823291 | 11/1979 |
| DE | 2946728 | 5/1981 |
| DE | 3143421 | 5/1982 |
| DE | 3045996 | 7/1982 |
| DE | 3120102 | 12/1982 |
| DE | 3510586 | 10/1986 |
| DE | 3604823 | 8/1987 |
| DE | 8712328 | 3/1988 |
| DE | 3711511 | 6/1988 |
| DE | 3904558 | 8/1990 |
| DE | 3942998 | 7/1991 |
| DE | 4238263 | 5/1993 |
| DE | 4303882 | 8/1994 |
| DE | 4339049 | 5/1995 |
| DE | 29616210 | 1/1997 |
| DE | 19608716 | 4/1997 |
| DE | 19751106 | 5/1998 |
| DE | 19717411 | 11/1998 |
| DE | 19751108 | 5/1999 |
| DE | 19801173 | 7/1999 |
| DE | 19848540 | 5/2000 |
| DE | 10224154 | 12/2003 |
| DE | 10310765 | 9/2004 |
| DE | 10328514 | 3/2005 |
| DE | 102004022206 | 12/2005 |
| DE | 202005015147 | 3/2006 |
| EP | 0 246 350 | 11/1987 |
| EP | 0 521 264 | 1/1993 |
| EP | 0 556 705 | 8/1993 |
| EP | 0 558 429 | 9/1993 |
| EP | 0 836 868 | 4/1998 |
| EP | 0 882 955 | 12/1998 |
| EP | 1 159 926 | 5/2001 |
| FR | 179 607 | 11/1906 |
| FR | 1 275 415 | 9/1960 |
| FR | 1 347 865 | 11/1963 |
| FR | 2 276 027 | 6/1974 |
| FR | 2 235 669 | 1/1975 |
| FR | 2 313 708 | 12/1976 |
| FR | 2 502 935 | 10/1982 |
| FR | 2 517 953 | 6/1983 |
| FR | 2 573 301 | 11/1984 |
| FR | 2 862 813 | 5/2005 |
| FR | 2 864 439 | 7/2005 |
| JP | 5-5106 | 1/1993 |
| JP | 05-40112 | 2/1993 |
| JP | 06343644 | 12/1994 |
| JP | 07265328 | 10/1995 |
| JP | 08056955 | 3/1996 |
| JP | 08252263 | 10/1996 |
| JP | 09000492 | 1/1997 |
| JP | 09010223 | 1/1997 |
| JP | 11244298 | 9/1999 |
| JP | 2000342599 | 12/2000 |
| JP | 2000350732 | 12/2000 |
| JP | 2001008944 | 1/2001 |
| JP | 2001029356 | 2/2001 |
| JP | 2001128990 | 5/2001 |
| JP | 2001231870 | 8/2001 |
| JP | 2008142467 | 6/2008 |
| SU | 166452 | 11/1964 |
| SU | 401367 | 11/1974 |
| SU | 727201 | 4/1980 |
| WO | WO97/41924 | 11/1997 |
| WO | WO00/47283 | 8/2000 |
| WO | WO01/74252 | 10/2001 |
| WO | WO2006/042117 | 4/2006 |
| WO | WO 2007112578 | 10/2007 |
| WO | WO2010/035831 | 9/2009 |

OTHER PUBLICATIONS

U.S. Appl. No. 08/483,742, filed Jun. 7, 1995.
U.S. Appl. No. 08/136,098, filed Oct. 14, 1993.

(56) References Cited

OTHER PUBLICATIONS

U.S. Appl. No. 12/389,906, filed Feb. 20, 2009.
U.S. Appl. No. 12/389,915, filed Feb. 20, 2009.
U.S. Appl. No. 12/401,268, filed Mar. 10, 2009.
U.S. Appl. No. 12/416,583, filed Apr. 1, 2009.
U.S. Appl. No. 12/423,609, filed Apr. 14, 2009.
U.S. Appl. No. 12/436,231, filed May 6, 2009.
U.S. Appl. No. 12/436,237, filed May 6, 2009.
U.S. Appl. No. 12/436,239, filed May 6, 2009.
U.S. Appl. No. 12/472,831, filed May 27, 2009.
U.S. Appl. No. 12/475,082, filed May 29, 2009.
U.S. Appl. No. 12/476,960, filed Jun. 2, 2009.
U.S. Appl. No. 12/487,917, filed Jun. 19, 2009.
U.S. Appl. No. 12/493,302, filed Jun. 29, 2009.
U.S. Appl. No. 12/504,738, filed Jun. 17, 2009.
U.S. Appl. No. 12/535,851, filed Aug. 5, 2009.
U.S. Appl. No. 12/535,856, filed Aug. 5, 2009.
U.S. Appl. No. 12/536,616, filed Aug. 6, 2009.
U.S. Appl. No. 12/542,348, filed Aug. 17, 2009.
U.S. Appl. No. 12/542,785, filed Aug. 18, 2009.
U.S. Appl. No. 12/547,155, filed Aug. 25, 2009.
U.S. Appl. No. 12/548,644, filed Aug. 27, 2009.
U.S. Appl. No. 12/555,576, filed Sep. 8, 2009.
U.S. Appl. No. 12/556,010, filed Sep. 9, 2009.
U.S. Appl. No. 12/556,238, filed Sep. 9, 2009.
U.S. Appl. No. 12/561,096, filed Sep. 16, 2009.
U.S. Appl. No. 12/562,575, filed Sep. 18, 2009.
U.S. Appl. No. 12/562,842, filed Sep. 18, 2009.
U.S. Appl. No. 12/566,299, filed Sep. 24, 2009.
U.S. Appl. No. 12/568,067, filed Sep. 28, 2009.
U.S. Appl. No. 12/568,524, filed Sep. 28, 2009.
U.S. Appl. No. 12/568,551, filed Sep. 28, 2009.
U.S. Appl. No. 12/568,777, filed Sep. 29, 2009.
U.S. Appl. No. 12/568,838, filed Sep. 29, 2009.
U.S. Appl. No. 12/568,883, filed Sep. 29, 2009.
U.S. Appl. No. 12/568,972, filed Sep. 29, 2009.
U.S. Appl. No. 12/569,171, filed Sep. 29, 2009.
U.S. Appl. No. 12/569,685, filed Sep. 29, 2009.
U.S. Appl. No. 12/582,857, filed Oct. 21, 2009.
U.S. Appl. No. 12/606,769, filed Oct. 27, 2009.
U.S. Appl. No. 12/607,221, filed Oct. 28, 2009.
U.S. Appl. No. 12/607,268, filed Oct. 28, 2009.
U.S. Appl. No. 12/619,323, filed Nov. 16, 2009.
U.S. Appl. No. 12/619,462, filed Nov. 16, 2009.
U.S. Appl. No. 12/620,289, filed Nov. 17, 2009.
U.S. Appl. No. 12/642,623, filed Dec. 18, 2009.
U.S. Appl. No. 12/686,726, filed Jan. 13, 2010.
U.S. Appl. No. 12/692,856, filed Jan. 25, 2010.
U.S. Appl. No. 12/696,671, filed Jan. 29, 2010.
U.S. Appl. No. 12/696,966, filed Jan. 29, 2010.
U.S. Appl. No. 12/701,030, filed Feb. 5, 2010.
U.S. Appl. No. 12/708,974, filed Feb. 19, 2010.
U.S. Appl. No. 12/709,014, filed Feb. 19, 2010.
U.S. Appl. No. 12/712,864, filed Feb. 25, 2010.
U.S. Appl. No. 12/713,429, filed Feb. 26, 2010.
U.S. Appl. No. 12/713,515, filed Feb. 26, 2010.
U.S. Appl. No. 12/713,641, filed Feb. 26, 2010.
U.S. Appl. No. 12/722,034, filed Mar. 11, 2010.
U.S. Appl. No. 12/731,367, filed Mar. 25, 2010.
U.S. Appl. No. 12/732,508, filed Mar. 26, 2010.
U.S. Appl. No. 12/732,521, filed Mar. 26, 2010.
U.S. Appl. No. 12/761,267, filed Apr. 15, 2010.
U.S. Appl. No. 12/769,457, filed Apr. 28, 2010.
U.S. Appl. No. 12/772,675, filed May 3, 2010.
U.S. Appl. No. 12/777,984, filed May 11, 2010.
U.S. Appl. No. 12/786,671, filed May 25, 2010.
U.S. Appl. No. 12/787,639, filed May 26, 2010.
U.S. Appl. No. 12/792,904, filed Jun. 3, 2010.
U.S. Appl. No. 12/792,932, filed Jun. 3, 2010.
U.S. Appl. No. 12/792,947, filed Jun. 3, 2010.
U.S. Appl. No. 12/792,970, filed Jun. 3, 2010.
U.S. Appl. No. 12/793,037, filed Jun. 3, 2010.
U.S. Appl. No. 12/819,330, filed Jun. 21, 2010.
U.S. Appl. No. 12/823,211, filed Jun. 25, 2010.
U.S. Appl. No. 12/826,902, filed Jun. 30, 2010.
Alexander et al., "Magnetic Resonance Image-Directed Stereotactic Neurosurgery: Use of Image Fusion with Computerized Tomography to Enhance Spatial Accuracy" Journal Neurosurgery, 83 (1995), pp. 271-276.
Anderson et al., "A Numerical Study of Rapid Heating for High Temperature Radio Frequency Hyperthermia" International Journal of Bio-Medical Computing, 35 (1994), pp. 297-307.
Anonymous. (1999) Auto Suture MIBB Site Marker: Single Use Clip Applier, United States Surgical (Product instructions), 2 pages.
Anonymous. (2001) Disposable Chiba Biopsy Needles and Trays, Biopsy and Special Purpose Needles Cook Diagnostic and Interventional Products Catalog (products list), 4 pages.
Anonymous. (1987) Homer Mammalok™ Breast Lesion Needle/Wire Localizer, Namic ® Angiographic Systems Division, Glens Falls, New York, (Hospital products price list), 4 pages.
Anonymous. (1999) MIBB Site Marker, United States Surgical (Sales brochure), 4 pages.
Anonymous. Blunt Tubes with Finished Ends. Pointed Cannula, Popper & Sons Biomedical Instrument Division, (Products Price List), one page, Jul. 19, 2000.
Anonymous. Ground Cannulae, ISPG, New Milford, CT, (Advertisement) one page, Jul. 19, 2000.
B. Levy M.D. et al., "Randomized Trial of Suture Versus Electrosurgical Bipolar Vessel Sealing in Vaginal Hysterectomy" Obstetrics & Gynecology, vol. 102, No. 1, Jul. 2003.
B. Levy M.D. et al., "Update on Hysterectomy New Technologies and Techniques" OBG Management, Feb. 2003.
B. Levy M.D., "Use of a New Vessel Ligation Device During Vaginal Hysterectomy" FIGO 2000, Washington, D.C.
B. F. Mullan et al., (May 1999) "Lung Nodules: Improved Wire for CT-Guided Localization," Radiology 211:561-565.
B. T. Heniford M.D. et al., "Initial Research and Clinical Results with an Electrothermal Bipolar Vessel Sealer" Oct. 1999.
Bergdahl et al., "Studies on Coagulation and the Development of an Automatic Computerized Bipolar Coagulator" Journal of Neurosurgery 75:1 (Jul. 1991), pp. 148-151.
Bulletin of the American Physical Society, vol. 47, No. 5, Aug. 2002, p. 41.
C. F. Gottlieb et al., "Interstitial Microwave Hyperthermia Applicators having Submillimetre Diameters", Int. J. Hyperthermia, vol. 6, No. 3, pp. 707-714, 1990.
C. H. Durney et al., "Antennas for Medical Applications", Antenna Handbook: Theory Application and Design, p. 24-40, Van Nostrand Reinhold, 1988 New York, V.T. Lo, S.W. Lee.
Carbonell et al., "Comparison of the Gyrus PlasmaKinetic Sealer and the Valleylab LigaSure™ Device in the Hemostasis of Small, Medium, and Large-Sized Arteries" Carolinas Laparoscopic and Advanced Surgery Program, Carolinas Medical Center, Charlotte, NC 2003.
Carus et al., "Initial Experience With the LigaSures™ Vessel Sealing System in Abdominal Surgery" Innovations That Work, Jun. 2002.
Chicharo et al., "A Sliding Goertzel Algorithm" Aug. 1996 DOS pp. 283-297 Signal Processing, Elsevier Science Publishers B.V. Amsterdam, NL, vol. 52, No. 3.
Chou, C.K., (1995) "Radiofrequency Hyperthermia in Cancer Therapy," Chapter 941n Biologic Effects of Nonionizing Electromagnetic Fields, CRC Press, Inc., pp. 1424-1428.
Chung et al., "Clinical Experience of Sutureless Closed Hemorrhoidectomy with LigaSure™" Diseases of the Colon & Rectum, vol. 46, No. 1, Jan. 2003.
Cosman et al., "Methods of Making Nervous System Lesions" In William RH, Rengachary SS (eds): Neurosurgery, New York: McGraw•Hill, vol. 111, (1984), pp. 2490-2499.
Cosman et al., "Radiofrequency Lesion Generation and its Effect on Tissue Impedence", Applied Neurophysiology, 51:230-242, 1988.
Cosman et al., "Theoretical Aspects of Radiofrequency Lesions in the Dorsal Root Entry Zone" Neurosurgery 15:(1984), pp. 945-950.

(56) References Cited

OTHER PUBLICATIONS

Crawford et al., "Use of the LigaSure™ Vessel Sealing System in Urologic Cancer Surger" Grand Rounds in Urology 1999, vol. 1, Issue 4, pp. 10-17.
Dulemba et al., "Use of a Bipolar Electrothermal Vessel Sealer in Laparoscopically Assisted Vaginal Hysterectomy" Sales/Product Literature; Jan. 2004.
E. David Crawford, "Evaluation of a New Vessel Sealing Device in Urologic Cancer Surgery" Sales/Product Literature 2000.
E. David Crawford, "Use of a Novel Vessel Sealing Technology in Management of the Dorsal Veinous Complex" Sales/Product Literature 2000.
Esterline, "Light Key Projection Keyboard" 2004 Advanced Input Systems, located at: <http://www.advanced-input.com/lightkey> last visited on Feb. 10, 2005.
Esterline Product Literature, "Light Key: Visualize a Virtual Keyboard. One With No Moving Parts", Nov. 1, 2003; 4 pages.
Geddes et al., "The Measurement of Physiologic Events by Electrical Impedence" Am. J. MI, Jan. Mar. 1964, pp. 16-27.
Goldberg et al., "Image-guided Radiofrequency Tumor Ablation: Challenges and Opportunities—Part I", (2001) J Vase. Interv. Radiol, vol. 12, pp. 1021-1032.
Goldberg et al. (1995) "Saline-enhanced RF Ablation: Demonstration of Efficacy and Optimization of Parameters", Radiology, 197(P): 140 (Abstr).
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
H. Schwarzmaier et al., "Magnetic Resonance Imaging of Microwave Induced Tissue Heating" Dept. of Laser Medicine & Dept. of Diagnostic Radiology; Heinrich-Heine-University, Duesseldorf, Germany; Dec. 8, 1994; pp. 729-731.
Heniford et al., "Initial Results with an Electrothermal Bipolar Vessel Sealer" Surgical Endoscopy (2001) 15:799-801.
Herman at al., "Laparoscopic Intestinal Resection With the LigaSure™ Vessel Sealing System: A Case Report" Innovations That Work, Feb. 2002.
Humphries Jr. et al., "Finite•Element Codes to Model Electrical Heating and Non•Llnear Thermal Transport in Biological Media", Proc. ASME HTD-355, 131 (1997).
Ian D. McRury et al., The Effect of Ablation Sequence and Duration on Lesion Shape Using Rapidly Pulsed Radiofrequency Energy Through Electrodes, Feb. 2000, Springer Netherlands, vol. 4; No. 1, pp. 307-320.
Jarrett et al., "Use of the LigaSure™ Vessel Sealing System for Peri-Hilar Vessels in Laparoscopic Nephrectomy" Sales/Product Literature 2000.
Johnson et al., "Evaluation of a Bipolar Electrothermal Vessel Sealing Device in Hemorrhoidectomy" Sales/Product Literature, Jan. 2004.
Johnson, "Evaluation of the LigaSure™ Vessel Sealing System in Hemorrhoidectormy" American College of Surgeons (ACS) Clinic La Congress Poster (2000).
Johnson et al., "New Low-Profile Applicators for Local Heating of Tissues", IEEE Transactions on Biomedical Engineering, vol., BME-31, No. 1, Jan. 1984, pp. 28-37.
Johnson, "Use of the LigaSure™ Vessel Sealing System in Bloodless Hemorrhoidectomy" Innovations That Work, Mar. 2000.
Joseph G. Andriole M.D. et al., "Biopsy Needle Characteristics Assessed in the Laboratory", Radiology 148: 659-662, Sep. 1983.
Joseph Ortenberg, "LigaSure™ System Used in Laparoscopic 1st and 2nd Stage Orchiopexy" Innovations That Work, Nov. 2002.
K. Ogata, Modern Control Engineering, Prentice-Hall, Englewood Cliffs, N.J., 1970.
Kennedy et al., "High-burst-strength, feedback-controlled bipolar vessel sealing" Surgical Endoscopy (1998) 12: 876-878.
Kopans, D.B. et al., (Nov. 1985) "Spring Hookwire Breast Lesion Localizer: Use with Rigid-Compression. Mammographic Systems," Radiology I57(2):537-538.

Koyle et al., "Laparoscopic Palomo Varicocele Ligation in Children and Adolescents" Pediatric Endosurgery & Innovative Techniques, vol. 6, No. 1, 2002.
LigaSure™ Vessel Sealing System, the Seal of Confidence in General, Gynecologic, Urologic, and Laparaoscopic Surgery, Sales/Product Literature, Jan. 2004.
Livraghi et al., (1995) "Saline-enhanced RF Tissue Ablation in the Treatment of Liver Metastases", Radiology, p. 140 (Abstr).
Lyndon B. Johnson Space Center, Houston, Texas, "Compact Directional Microwave Antenna for Localized Heating," NASA Tech Briefs, Mar. 2008.
M. A. Astrahan, "A Localized Current Field Hyperthermia System for Use with 192-Iridium Interstitial Implants" Medical Physics. 9(3), May/Jun. 1982.
Magdy F. Iskander et al., "Design Optimization of Interstitial Antennas", IEEE Transactions on Biomedical Engineering, vol. 36, No. 2, Feb. 1989, pp. 238-246.
McGahan et al., (1995) "Percutaneous Ultrasound-guided Radiofrequency Electrocautery Ablation of Prostate Tissue in Dogs", Acad Radiol, vol. 2, No. 1: pp. 61-65.
McLellan et al., "Vessel Sealing for Hemostasis During Pelvic Surgery" Int'l Federation of Gynecology and Obstetrics FIGO World Congress 2000, Washington, DC.
MDTECH product literature (Dec. 1999) "FlexStrand": product description, 1 page.
MDTECH product literature (Mar. 2000) I'D Wire: product description, 1 page.
Medtrex Brochure "The O.R. Pro 300" 1 page, Sep. 1998.
Michael Choti, "Abdominoperineal Resection with the LigaSure™ Vessel Sealing System and LigaSure™ Atlas 20 cm Open Instrument" Innovations That Work, Jun. 2003.
Muller et al., "Extended Left Hemicolectomy Using the LigaSure™ Vessel Sealing System" Innovations That Work. LJ, Sep. 1999.
Murakami, R. et al., (1995). "Treatment of Hepatocellular Carcinoma: Value of Percutaneous Microwave Coagulation," American Journal of Radiology (AJR) 164:1159-1164.
Ni Wei et al., "A Signal Processing Method for the Coriolis Mass Flowmeter Based on a Normalized . . . " Journal of Applied Sciences•Yingyong Kexue Xuebao, Shangha CN, vol. 23, No. 2:(Mar. 2005); pp. 160-184.
Ogden, "Goertzel Alternative to the Fourier Transform" Jun. 1993 pp. 485-487 Electronics World; Reed Business Publishing, Sutton, Surrey, BG, vol. 99, No. 9, 1687.
Olsson M.D. et al., "Radical Cystectomy in Females" Current Surgical Techniques in Urology, vol. 14, Issue 3, 2001.
Organ, L W., "Electrophysiologic Principles of Radiofrequency Lesion Making" Appl. Neurophysiol, vol. 39: pp. 69-76 (1976/77).
P.R. Stauffer et al., "Interstitial Heating Technologies", Thermoradiotheray and Thermochemotherapy (1995) vol. I, Biology, Physiology, Physics, pp. 279-320.
Palazzo et al., "Randomized clinical trial of LigaSure™ versus open haemorrhoidectomy" British Journal of Surgery 2002,89,154-157 "Innovations in Electrosurgery" Sales/Product Literature; Dec. 31, 2000.
Paul G. Horgan, "A Novel Technique for Parenchymal Division During Hepatectomy" The American Journal of Surgery, vol. 181, No. 3, Apr. 2001, pp. 236-237.
Peterson et al., "Comparison of Healing Process Following Ligation with Sutures and Bipolar Vessel Sealing" Surgical Technology International (2001).
R. Gennari et al (Jun. 2000) "Use of Technetium-99m-Labeled Colloid Albumin for Preoperative and Intraoperative Localization of Non palpable Breast Lesions," American College of Surgeons. 190(6):692-699.
Valleylab Brochure, "Reducing Needlestick Injuries in the Operating Room" 1 page, Mar. 2001.
Reidenbach, (1995) "First Experimental Results with Special Applicators for High-Frequency Interstitial Thermotherapy", Society Minimally Invasive Therapy, 4(Suppl 1):40 (Abstr).
Richard Wolf Medical Instruments Corp. Brochure, "Kleppinger Bipolar Forceps & Bipolar Generator" 3 pages, Jan. 1989.

(56) References Cited

OTHER PUBLICATIONS

Rothenberg et al., "Use of the LigaSure™ Vessel Sealing System in Minimally Invasive Surgery in Children" Int'l Pediatric Endosurgery Group (I PEG) 2000.
Sayfan et al., "Sutureless Closed Hemorrhoidectomy: A New Technique" Annals of Surgery, vol. 234, No. 1, Jul. 2001, pp. 21-24.
Sengupta et al., "Use of a Computer-Controlled Bipolar Diathermy System in Radical Prostatectomies and Other Open Urological Surgery" ANZ Journal of Surgery (2001) 71.9 pp. 538-540.
Sigel et al., "The Mechanism of Blood Vessel Closure by High Frequency Electrocoagulation" Surgery Gynecology & Obstetrics, Oct. 1965 pp. 823-831.
Solbiati et al., (2001) "Percutaneous Radio-frequency Ablation of Hepatic Metastases from Colorectal Cancer: Long-term Results in 117 Patients", Radiology, vol. 221, pp. 159-166.
Solbiati et al. (1995) "Percutaneous US-guided RF Tissue Ablation of Liver Metastases: Long-term Follow-up", Radiology, pp. 195-203.
Strasberg et at., "Use of a Bipolar Vassel-Sealing Device for Parenchymal Transection During Liver Surgery" Journal of Gastrointestinal Surgery, vol. 6, No. 4, Jul./Aug. 2002 pp. 569-574.
Stuart W. Young, Nuclear Magnetic Resonance Imaging—Basic Principles, Raven Press, New York, 1984.
Sugita et al., "Bipolar Coagulator with Automatic Thermocontrol" J. Neurosurg., vol. 41, Dec. 1944, pp. 777-779.
Sylvain Labonte et al., "Monopole Antennas for Microwave Catheter Ablation", IEEE Trans. on Microwave Theory and Techniques, vol. 44, No. 10, pp. 1832-1840, Oct. 1995.
T. Matsukawa et al., "Percutaneous Microwave Coagulation Therapy in Liver Tumors", Acta Radiologica, vol. 38, pp. 410-415, 1997.
T. Seki et al., (1994) "Ultrasonically Guided Percutaneous Microwave Coagulation Therapy for Small Hepatocellular Carcinoma," Cancer 74(3):817.825.
Urologix, Inc.—Medical Professionals: Targis™ Technology (Date Unknown). "Overcoming the Challenge" located at: <http://www.urologix.com!medicaUtechnology.html > last visited on Apr. 27, 2001, 3 pages.
Urrutia et al., (1988). "Retractable-Barb Needle for Breast Lesion Localization: Use in 60 Cases," Radiology 169(3):845-847.
Valleylab Brochure, "Valleylab Electroshield Monitoring System" 2 pages, Nov. 1995.
ValleyLab Brochure, "Electosurgery: A Historical Overview", Innovations in Electrosurgery, 1999.
Vallfors et al., "Automatically Controlled Bipolar Electrocoagulation—'COA-COMP'" Neurosurgical Review 7:2-3 (1984) pp. 187-190.
W. Scott Helton, "LigaSure™ Vessel Sealing System: Revolutionary Hemostasis Product for General Surgery" Sales/Product Literature 1999.
Wald et al., "Accidental Burns", JAMA, Aug. 16, 1971, vol. 217, No. 7, pp. 916-921.
Walt Boyles, "Instrumentation Reference Book", 2002, Butterworth-Heinemann, pp. 262-264.
Wonnell et al., "Evaluation of Microwave and Radio Frequency Catheter Ablation in a Myocardium-Equivalent Phantom Model", IEEE Transactions on Biomedical Engineering, vol. 39, No. 10, Oct. 1992; pp. 1086-1095.
European Search Report EP 98300964.8 dated Dec. 13, 2000.
European Search Report EP 98944778 dated Nov. 7, 2000.
European Search Report EP 98958575.7 dated Oct. 29, 2002.
European Search Report EP 02786604.5 dated Feb. 10, 2010.
European Search Report EP 03721482 dated Feb. 6, 2006.
European Search Report EP 04009964 dated Jul. 28, 2004.
European Search Report EP 04013772 dated Apr. 11, 2005.
European Search Report EP 04015980 dated Nov. 3, 2004.
European Search Report EP 04015981.6 dated Oct. 25, 2004.
European Search Report EP 04027314 dated Mar. 31, 2005.
European Search Report EP 04027479 dated Mar. 17, 2005.
European Search Report EP 04027705 dated Feb. 10, 2005.
European Search Report EP 04710258 dated Oct. 15, 2004.
European Search Report EP 04752343.6 dated Jul. 31, 2007.
European Search Report EP 04778192,7 dated Jul. 1, 2009.
European Search Report EP 05002027.0 dated May 12, 2005.
European Search Report EP 05002769.7 dated Jun. 19, 2006.
European Search Report EP 05013463.4 dated Oct. 7, 2005.
European Search Report EP 05013895 dated Oct. 21, 2005.
European Search Report EP 05014156.3 dated Jan. 4, 2006.
European Search Report EP 05016399 dated Jan. 13, 2006.
European Search Report EP 05017281 dated Nov. 24, 2005.
European Search Report EP 05019130.3 dated Oct. 27, 2005.
European Search Report EP 05019882 dated Feb. 16, 2006.
European Search Report EP 05020665.5 dated Feb. 27, 2006.
European Search Report EP 05020666.3 dated Feb. 27, 2006.
European Search Report EP 05021025.1 dated Mar. 13, 2006.
European Search Report EP 05021197.8 dated Feb. 20, 2006.
European Search Report EP 05021777 dated Feb. 23, 2006.
European Search Report EP 05021779.3 dated Feb. 2, 2006.
European Search Report EP 05021780.1 dated Feb. 23, 2006.
European Search Report EP 05021935 dated Jan. 27, 2006.
European Search Report EP 05021936.9 dated Feb. 6, 2006.
European Search Report EP 05021937.7 dated Jan. 23, 2006.
European Search Report EP 05021939 dated Jan. 27, 2006.
European Search Report EP 05021944.3 dated Jan. 25, 2006.
European Search Report EP 05022350.2 dated Jan. 30, 2006.
European Search Report EP 05023017.6 dated Feb. 24, 2006.
European Search Report EP 05025423.4 dated Jan. 19, 2007.
European Search Report EP 05025424 dated Jan. 30, 2007.
European Search Report EP 05810523 dated Jan. 29, 2009.
European Search Report EP 06000708.5 dated May 15, 2006.
European Search Report EP 06002279.5 dated Mar. 30, 2006.
European Search Report EP 06005185.1 dated May 10, 2006.
European Search Report EP 06005540 dated Sep. 24, 2007.
European Search Report EP 06006717.0 dated Aug. 11, 2006.
European Search Report EP 06006961 dated Oct. 22, 2007.
European Search Report EP 06006963 dated Jul. 25, 2006.
European Search Report EP 06008779.8 dated Jul. 13, 2006.
European Search Report EP 06009435 dated Jul. 13, 2006.
European Search Report EP 06010499.9 dated Jan. 29, 2008.
European Search Report EP 06014461.5 dated Oct. 31, 2006.
European Search Report EP 06018206.0 dated Oct. 20, 2006.
European Search Report EP 06019768 dated Jan. 17, 2007.
European Search Report EP 06020574.7 dated Oct. 2, 2007.
European Search Report EP 06020583.8 dated Feb. 7, 2007.
European Search Report EP 06020584.6 dated Feb. 1, 2007.
European Search Report EP 06020756.0 dated Feb. 16, 2007.
European Search Report EP 06022028.2 dated Feb. 13, 2007.
European Search Report EP 06023756.7 dated Feb. 21, 2008.
European Search Report EP 06024122.1 dated Apr. 16, 2007.
European Search Report EP 06024123.9 dated Mar. 6, 2007.
European Search Report EP 06025700.3 dated Apr. 12, 2007.
European Search Report EP 07000885.9 dated May 15, 2007.
European Search Report EP 07001480.8 dated Apr. 19, 2007.
European Search Report EP 07001481.6 dated May 2, 2007.
European Search Report EP 07001485.7 dated May 23, 2007.
European Search Report EP 07001488.1 dated Jun. 5, 2007.
European Search Report EP 07001489.9 dated Dec. 20, 2007.
European Search Report EP 07001491 dated Jun. 6, 2007.
European Search Report EP 07001527.6 dated May 18, 2007.
European Search Report EP 07007783.9 dated Aug. 14, 2007.
European Search Report EP 07008207.8 dated Sep. 13, 2007.
European Search Report EP 07009026.1 dated Oct. 8, 2007.
European Search Report EP 07009028 dated Jul. 16, 2007.
European Search Report EP 07009029.5 dated Jul. 20, 2007.
European Search Report EP 07009321.6 dated Aug. 28, 2007.
European Search Report EP 07009322.4 dated Jan. 14, 2008.
European Search Report EP 07010672.9 dated Oct. 16, 2007.
European Search Report EP 07010673.7 dated Oct. 5, 2007.
European Search Report EP 07013779.9 dated Oct. 26, 2007.
European Search Report EP 07015191.5 dated Jan. 23, 2007.
European Search Report EP 07015601.3 dated Jan. 4, 2007.
European Search Report EP 07015602.1 dated Dec. 20, 2007.
European Search Report EP 07018375.1 dated Jan. 8, 2008.
European Search Report EP 07018821 dated Jan. 14, 2008.
European Search Report EP 07019173.9 dated Feb. 12, 2008.

(56) References Cited

OTHER PUBLICATIONS

European Search Report EP 07019174.7 dated Jan. 29, 2008.
European Search Report EP 07019178.8 dated Feb. 12, 2008.
European Search Report EP 07020283.3 dated Feb. 5, 2008.
European Search Report EP 07253835.8 dated Dec. 20, 2007.
European Search Report EP 08001019 dated Sep. 23, 2008.
European Search Report EP 08004975 dated Jul. 24, 2008.
European Search Report EP 08006731.7 dated Jul. 29, 2008.
European Search Report EP 08006733 dated Jul. 7, 2008.
European Search Report EP 08006734.1 dated Aug. 18, 2008.
European Search Report EP 08006735.8 dated Jan. 8, 2009.
European Search Report EP 08011282 dated Aug. 14, 2009.
European Search Report EP 08011705 dated Aug. 20, 2009.
European Search Report EP 08011705.4 extended dated Nov. 4, 2009.
European Search Report EP 08012829.1 dated Oct. 29, 2008.
European Search Report EP 08015842 dated Dec. 5, 2008.
European Search Report EP 08019920.1 dated Mar. 27, 2009.
European Search Report EP 08020530.5 dated May 27, 2009.
European Search Report EP 08169973.8 dated Apr. 6, 2009.
European Search Report EP 09010873.9 extended dated Nov. 13, 2009.
European Search Report EP 09010877.0 extended dated Dec. 3, 2009.
European Search Report EP 09151621 dated Jun. 18, 2009.
European Search Report EP 09156861.8 dated Aug. 4, 2009.
European Search Report EP 09161502.1 dated Sep. 2, 2009.
European Search Report EP 09161502.1 extended dated Oct. 30, 2009.
European Search Report EP 09165976.3 extended dated Mar. 17, 2010.
European Search Report EP 09166708 dated Oct. 15, 2009.
European Search Report EP 09166708.9 dated Mar. 18, 2010.
European Search Report EP 09169376.2 extended dated Dec. 16, 2009.
European Search Report EP 09172188.6 extended dated Apr. 23, 2010.
European Search Report EP 09172838.6 extended dated Jan. 20, 2010.
European Search Report EP 09173268.5 extended dated Jan. 27, 2010.
European Search Report EP 10158944.8 extended dated Jun. 21, 2010.
European Search Report EP 10161722.3 extended dated Jun. 16, 2010.
International Search Report PCT/US98/18640 dated Jan. 29, 1998.
International Search Report PCT/US98/23950 dated Jan. 14, 1998.
International Search Report PCT/US99/24869 dated Feb. 11, 2000.
International Search Report PCT/US01/11218 dated Aug. 14, 2001.
International Search Report PCT/US01/11224 dated Nov. 13, 2001.
International Search Report PCT/US01/11340 dated Aug. 16, 2001.
International Search Report PCT/US01/11420 dated Oct. 16, 2001.
International Search Report PCT/US02/01890 dated Jul. 25, 2002.
International Search Report PCT/US02/11100 dated Jul. 16, 2002.
International Search Report PCT/US03/09483 dated Aug. 13, 2003.
International Search Report PCT/US03/22900 dated Dec. 2, 2003.
International Search Report PCT/US03/37110 dated Jul. 25, 2005.
International Search Report PCT/US03/37111 dated Jul. 28, 2004.
International Search Report PCT/US03/37310 dated Aug. 13, 2004.
International Search Report PCT/US04/04685 dated Aug. 27, 2004.
International Search Report PCT/US04/13273 dated Dec. 15, 2004.
International Search Report PCT/US04/15311 dated Jan. 12, 2004.
International Search Report PCT/US05/36168 dated Aug. 28, 2006.
International Search Report PCT/US08/052460 dated Apr. 24, 2008.
International Search Report PCT/US09/31658 dated Mar. 11, 2009.
Miyakawa M et al, "Visualization and 3-D measurement of local SAR using a gel phantom", Electromagnetic Compatibility Aug. 24-28, 1998. IEEE Int. Symposium on Denver, CO USA.
T Larson: "Contrasting Heating Patterns and Efficiency of the Prostatron and Targis Microwave Antennae for Thermal Treatment of Benign Prostatic Hyperplasia", Jun. 1, 1998.
Vitkin I A et al: "Magnetic resonance imaging of temperature changes during interstitial microwave heating: A phantom study", Medical Physics, AIP, Melville, NY, US, Feb. 1, 1997.
Li D J et al: "Design and thermometry of an intracavitary microwave applicator suitable for treatment of some vaginal and rectal cancers", Nov. 1, 1984, Int. Journ of Radiation.
International Search Report EP11168657.2 dated Sep. 9, 2011.
International Search Report EP11168658.0 dated Sep. 12, 2011.
International Search Report EP11168659.8 dated Sep. 27, 2011.
Lee D J et al "A new design of microwave interstitial applicators for hyperthermia with improved treatment of volume", Int'l Jrnl of Radition; Oncology Biology Physics, 1986.

* cited by examiner

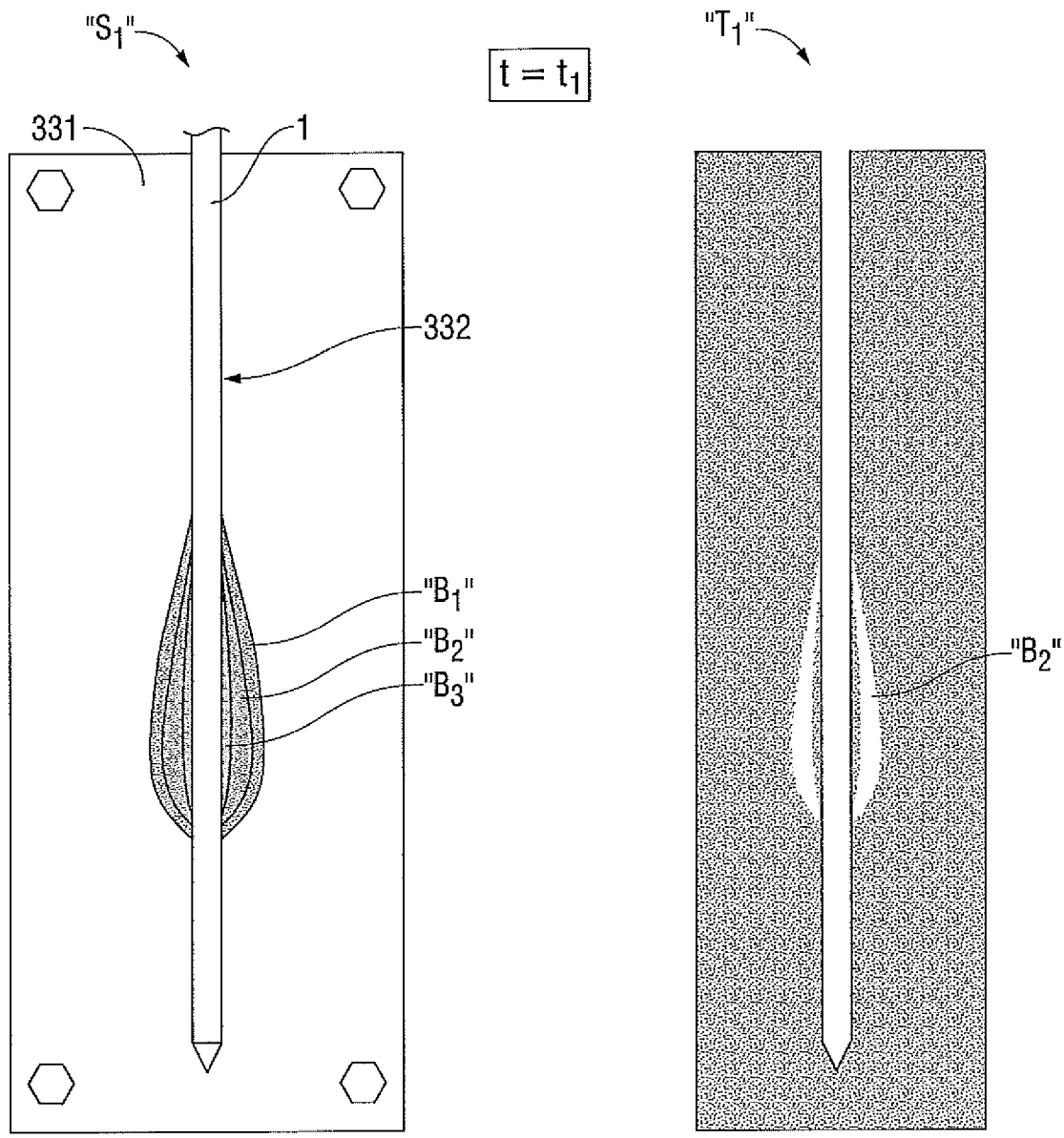

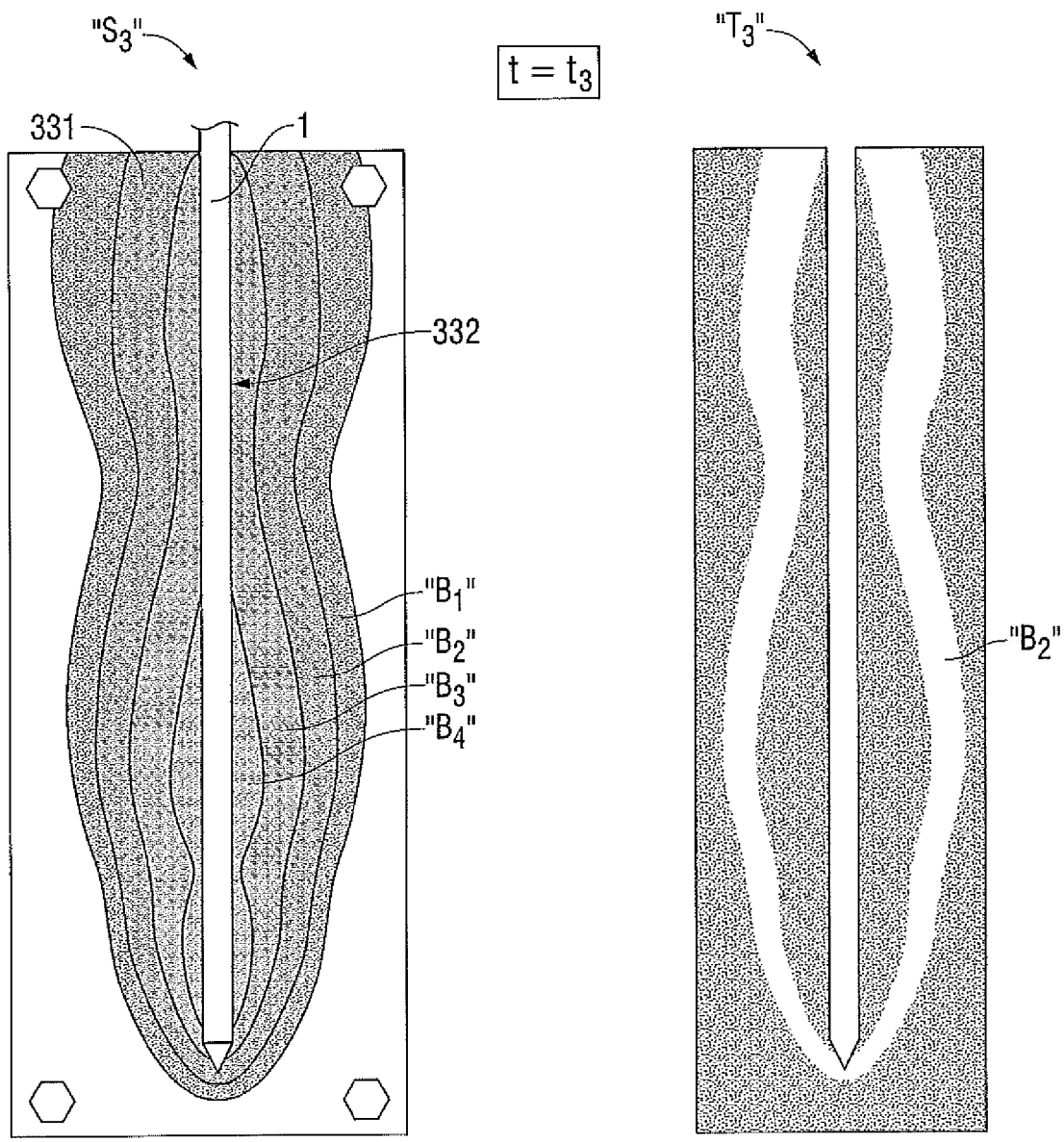

SPECIFIC ABSORPTION RATE MEASUREMENT AND ENERGY-DELIVERY DEVICE CHARACTERIZATION USING THERMAL PHANTOM AND IMAGE ANALYSIS

BACKGROUND

1. Technical Field

The present disclosure relates to a system and method for measuring the specific absorption rate of electromagnetic energy emitted by energy-delivery devices, such as energy-emitting probes or electrodes, and, more particularly, to specific absorption rate measurement and characterization of energy-delivery devices using a thermal phantom and image analysis.

2. Discussion of Related Art

Treatment of certain diseases requires the destruction of malignant tissue growths, e.g., tumors. Electromagnetic radiation can be used to heat and destroy tumor cells. Treatment may involve inserting ablation probes into tissues where cancerous tumors have been identified. Once the probes are positioned, electromagnetic energy is passed through the probes into surrounding tissue.

In the treatment of diseases such as cancer, certain types of tumor cells have been found to denature at elevated temperatures that are slightly lower than temperatures normally injurious to healthy cells. Known treatment methods, such as hyperthermia therapy, heat diseased cells to temperatures above 41° C. while maintaining adjacent healthy cells below the temperature at which irreversible cell destruction occurs. These methods involve applying electromagnetic radiation to heat, ablate and/or coagulate tissue. Microwave energy is sometimes utilized to perform these methods. Other procedures utilizing electromagnetic radiation to heat tissue also include coagulation, cutting and/or ablation of tissue. Many procedures and types of devices utilizing electromagnetic radiation to heat tissue have been developed.

In treatment methods utilizing electromagnetic radiation, such as hyperthermia therapy, the transference or dispersion of heat generally may occur by mechanisms of radiation, conduction, and convection. Biological effects that result from heating of tissue by electromagnetic energy are often referred to as "thermal" effects. "Thermal radiation" and "radiative heat transfer" are two terms used to describe the transfer of energy in the form of electromagnetic waves (e.g., as predicted by electromagnetic wave theory) or photons (e.g., as predicted by quantum mechanics). In the context of heat transfer, the term "conduction" generally refers to the transfer of energy from more energetic to less energetic particles of substances due to interactions between the particles. The term "convection" generally refers to the energy transfer between a solid surface and an adjacent moving fluid. Convection heat transfer may be a combination of diffusion or molecular motion within the fluid and the bulk or macroscopic motion of the fluid.

The extent of tissue heating may depend on several factors including the rate at which energy is absorbed by, or dissipated in, the tissue under treatment. The electromagnetic-energy absorption rate in biological tissue may be quantified by the specific absorption rate (SAR), a measure of the energy per unit mass absorbed by tissue and is usually expressed in units of watts per kilogram (W/kg). For SAR evaluation, a simulated biological tissue or "phantom" having physical properties, e.g., dielectric constant, similar to that of the human body is generally used.

One method to determine the SAR is to measure the rate of temperature rise in tissue as a function of the specific heat capacity (often shortened to "specific heat") of the tissue. This method requires knowledge of the specific heat of the tissue. A second method is to determine the SAR by measuring the electric field strength in tissue. This method requires knowledge of the conductivity and density values of the tissue.

The relationship between radiation and SAR may be expressed as $$SAR = \frac{1}{2}\frac{\sigma}{\rho}|E|^2, \quad (1)$$

where σ a is the tissue electrical conductivity in units of Siemens per meter (S/m), ρ is the tissue density in units of kilograms per cubic meter (kg/m³), and |E| is the magnitude of the local electric field in units of volts per meter (V/m).

The relationship between the initial temperature rise ΔT (° C.) in tissue and the specific absorption rate may be expressed as $$\Delta T = \frac{1}{c} SAR \Delta t, \quad (2)$$

where c is the specific heat of the tissue (or phantom material) in units of Joules/kg-° C., and Δt is the time period of exposure in seconds. Substituting equation (1) into equation (2) yields a relation between the induced temperature rise in tissue and the applied electric field as $$\Delta T = \frac{1}{2}\frac{\sigma}{\rho c}|E|^2 \Delta t. \quad (3)$$

As can be seen from the above equations, modifying the local electric-field amplitude directly affects the local energy absorption and induced temperature rise in tissue. In treatment methods such as hyperthermia therapy, it would be desirable to deposit an electric field of sufficient magnitude to heat malignant tissue to temperatures above 41° C. while limiting the SAR magnitude in nearby healthy tissue to be less than that within the tumor to keep the healthy cells below the temperature causing cell death.

SAR measurement and the characterization of energy-delivery devices may ensure clinical safety and performance of the energy-delivery devices. SAR measurement and characterization of energy-delivery devices may generate data to facilitate planning and effective execution of therapeutic hyperthermic treatments.

SUMMARY

The present disclosure relates to a method of predicting a radiation pattern emitted by an energy applicator including the steps of providing thermal profile data for an energy applicator, determining a specific absorption rate around the energy applicator as a function of the thermal profile data, and generating a simulated radiation pattern for the energy applicator as a function of the determined specific absorption rate.

The present disclosure also relates to a method of analyzing time-series image data to determine the specific absorption rate around an energy applicator including the initial steps of acquiring time-series image data associated with an energy applicator and selecting a color band of the time-series image data. The method includes the step of thresholding the time-series image data to detect an inner boundary and an outer boundary of the selected color band in each image data of the time-series image data. The method also includes the steps of determining a change in temperature as a function of positional transition of the inner boundary and the outer boundary of the selected color band in each image data of the thresholded time-series image data, and calculating a specific absorption rate around the energy applicator as a function of the determined change in temperature.

BRIEF DESCRIPTION OF THE DRAWINGS

Objects and features of the presently disclosed system and method for specific absorption rate measurement and characterization of energy-delivery devices, the presently disclosed electrosurgical system and method for predicting a radiation pattern emitted by an energy applicator, and the presently disclosed method of analyzing time-series image data to determine the specific absorption rate around an energy applicator will become apparent to those of ordinary skill in the art when descriptions of various embodiments thereof are read with reference to the accompanying drawings, of which:

FIG. 10 is a schematic diagram illustrating the thermally-sensitive medium of the thermal profiling system of FIG. 9 during operation according to an embodiment of the present disclosure shown with a schematically-illustrated representation of a thermal radiation pattern formed on the thermally-sensitive medium at time t equal to $t_1$;

FIG. 11 is a schematic diagram illustrating a thresholded pattern image of a portion of the thermally-sensitive medium of FIG. 10 showing a selected temperature band at time t equal to $t_1$ according to an embodiment of the present disclosure;

FIG. 14 is a schematic diagram illustrating the thermally-sensitive medium of the thermal profiling system of FIG. 9 during operation according to an embodiment of the present disclosure shown with a schematically-illustrated representation of a thermal radiation pattern formed on the thermally-sensitive medium at time t equal to $t_3$;

FIG. 15 is a schematic diagram illustrating a thresholded pattern image of a portion of the thermally-sensitive medium of FIG. 14 showing a selected temperature band at time t equal to $t_3$ according to an embodiment of the present disclosure;

DETAILED DESCRIPTION

Figure 1:
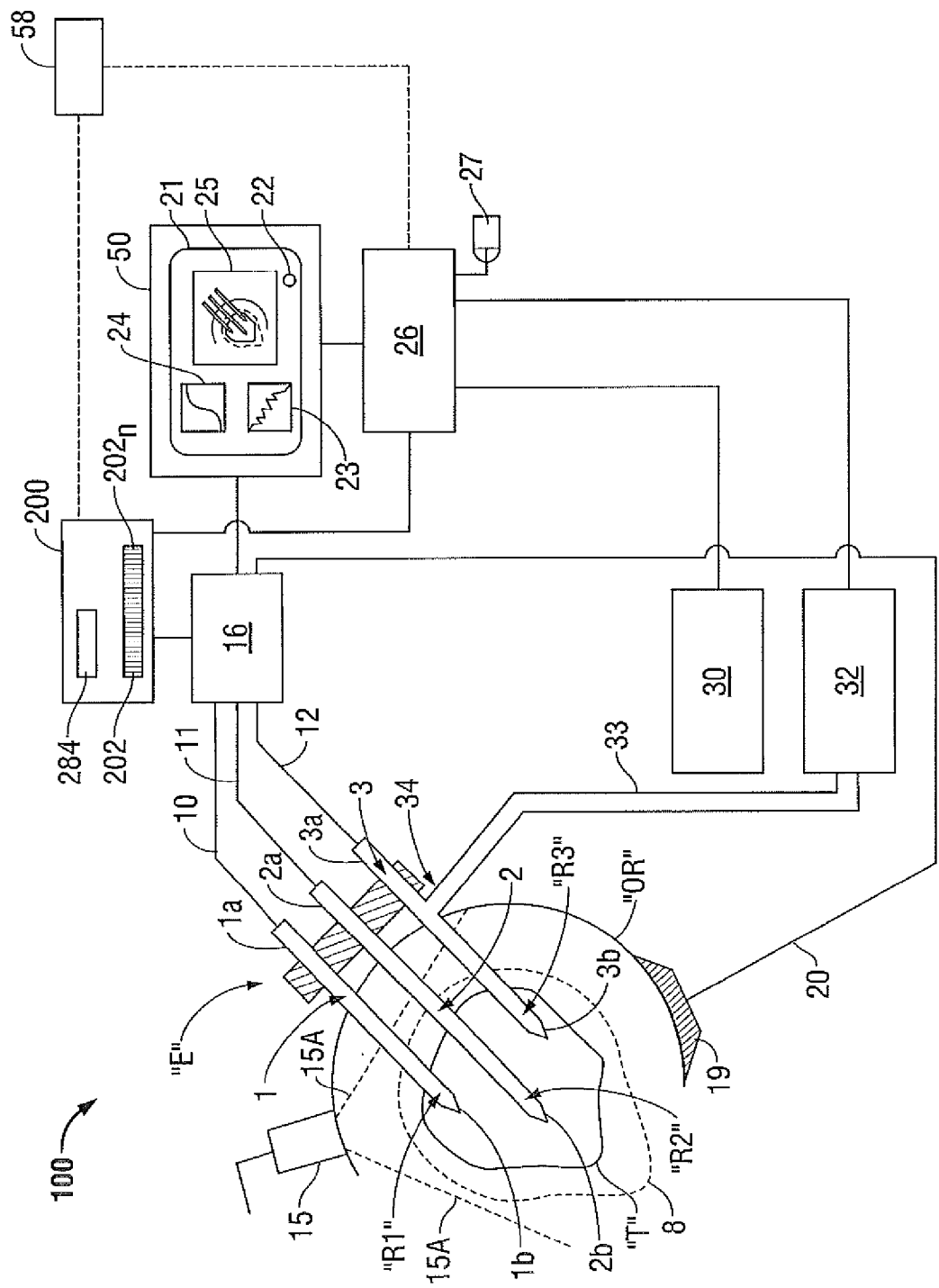
FIG. 1 is a schematic illustration of a thermal profiling system including an energy applicator array positioned for the delivery of energy to a targeted tissue area according to an embodiment of the present disclosure.

Hereinafter, embodiments of the system and method for specific absorption rate (SAR) measurement and characterization of energy-delivery devices of the present disclosure, the presently disclosed method of predicting a radiation pattern emitted by an energy applicator, and the presently disclosed method of analyzing time-series image data to determine the specific absorption rate around an energy applicator are described with reference to the accompanying drawings. Like reference numerals may refer to similar or identical elements throughout the description of the figures. As shown in the drawings and as used in this description, and as is traditional when referring to relative positioning on an object, the term "proximal" refers to that portion of the apparatus, or component thereof, closer to the user and the term "distal" refers to that portion of the apparatus, or component thereof, farther from the user.

This description may use the phrases "in an embodiment," "in embodiments," "in some embodiments," or "in other embodiments," which may each refer to one or more of the same or different embodiments in accordance with the present disclosure. For the purposes of this description, a phrase in the form "NB" means A or B. For the purposes of the description, a phrase in the form "A and/or B" means "(A), (B), or (A and B)". For the purposes of this description, a phrase in the form "at least one of A, B, or C" means "(A), (B), (C), (A and B), (A and C), (B and C), or (A, B and C)".

Electromagnetic energy is generally classified by increasing energy or decreasing wavelength into radio waves, microwaves, infrared, visible light, ultraviolet, X-rays and gamma-rays. As it is used in this description, "microwave" generally refers to electromagnetic waves in the frequency range of 300 megahertz (MHz) ($3 \times 10^8$ cycles/second) to 300 gigahertz (GHz) ($3 \times 10^{11}$ cycles/second). As it is used in this description, "ablation procedure" generally refers to any ablation procedure, such as microwave ablation, radio frequency (RF) ablation or microwave ablation assisted resection. As it is used in this description, "energy applicator" generally refers to any device that can be used to transfer energy from a power generating source, such as a microwave or RF electrosurgical generator, to tissue. As it is used in this description, "transmission line" generally refers to any transmission medium that can be used for the propagation of signals from one point to another.

As it is used in this description, "length" may refer to electrical length or physical length. In general, electrical length is an expression of the length of a transmission medium in terms of the wavelength of a signal propagating within the medium. Electrical length is normally expressed in terms of wavelength, radians or degrees. For example, electrical length may be expressed as a multiple or sub-multiple of the wavelength of an electromagnetic wave or electrical signal propagating within a transmission medium. The wavelength may be expressed in radians or in artificial units of angular measure, such as degrees. The electric length of a transmission medium may be expressed as its physical length multiplied by the ratio of (a) the propagation time of an electrical or electromagnetic signal through the medium to (b) the propagation time of an electromagnetic wave in free space over a distance equal to the physical length of the medium. The electrical length is in general different from the physical length. By the addition of an appropriate reactive element (capacitive or inductive), the electrical length may be made significantly shorter or longer than the physical length.

As used in this description, the term "real-time" means generally with no observable latency between data processing and display. As used in this description, "near real-time" generally refers to a relatively short time span between the time of data acquisition and display.

Various embodiments of the present disclosure provide systems and methods of directing energy to tissue in accordance with specific absorption rate data associated with an energy applicator. Embodiments may be implemented using electromagnetic radiation at microwave frequencies or at other frequencies. An electromagnetic energy delivery device including an energy applicator array, according to various embodiments, is designed and configured to operate between about 300 MHz and about 10 GHz.

Various embodiments of the presently disclosed electrosurgical system including an energy applicator, or energy applicator array, are suitable for microwave ablation and for use to pre-coagulate tissue for microwave ablation assisted surgical resection. In addition, although the following description describes the use of a dipole microwave antenna, the teachings of the present disclosure may also apply to a monopole, helical, or other suitable type of microwave antenna (or RF electrodes).

An electrosurgical system 100 according to an embodiment of the present disclosure is shown in FIG. 1 and includes an electromagnetic energy delivery device or energy applicator array "E". Energy applicator array "E" may include one or more energy applicators or probes. Probe thickness may be minimized, e.g., to reduce trauma to the surgical site and facilitate accurate probe placement to allow surgeons to treat target tissue with minimal damage to surrounding healthy tissue. In some embodiments, the energy applicator array "E" includes a plurality of probes. The probes may have similar or different diameters, may extend to equal or different lengths, and may have a distal end with a tapered tip. In some embodiments, the one or more probes may be provided with a coolant chamber. The probe(s) may be integrally associated with a hub (e.g., hub 34 shown in FIG. 1) that provides electrical and/or coolant connections to the probe(s). Additionally, or alternatively, the probe(s) may include coolant inflow and outflow ports to facilitate the flow of coolant into, and out of, the coolant chamber. Examples of coolant chamber and coolant inflow and outflow port embodiments are disclosed in commonly assigned U.S. patent application Ser. No. 12/401, 268 filed on Mar. 10, 2009, entitled "COOLED DIELECTRICALLY BUFFERED MICROWAVE DIPOLE ANTENNA", and U.S. Pat. No. 7,311,703, entitled "DEVICES AND METHODS FOR COOLING MICROWAVE ANTENNAS".

In the embodiment shown in FIG. 1, the energy applicator array "E" includes three probes 1, 2 and 3 having different lengths and arranged substantially parallel to each other. Probes 1, 2 and 3 generally include a radiating section "R1", "R2" and "R3", respectively, operably connected by a feedline (or shaft) 1a, 2a and 3a, respectively, to an electrosurgical power generating source 16, e.g., a microwave or RF electrosurgical generator. Transmission lines 10, 11 and 12 may be provided to electrically couple the feedlines 1a, 2a and 3a, respectively, to the electrosurgical power generating source 16. Located at the distal end of each probe 1, 2 and 3 is a tip portion 1b, 2b and 3b, respectively, which may be configured to be inserted into an organ "OR" of a human body or any other body tissue. Tip portion 1b, 2b and 3b may terminate in a sharp tip to allow for insertion into tissue with minimal resistance. Tip portion 1b, 2b and 3b may include other shapes, such as, for example, a tip that is rounded, flat, square, hexagonal, or cylindroconical. The shape, size and number of probes of the energy applicator array "E" may be varied from the configuration depicted in FIG. 1.

Electrosurgical system 100 according to embodiments of the present disclosure includes a user interface 50 that may include a display device 21, such as without limitation a flat panel graphic LCD (liquid crystal display), adapted to visually display one or more user interface elements (e.g., 23, 24 and 25 shown in FIG. 1). In an embodiment, the display device 21 includes touchscreen capability, e.g., the ability to receive user input through direct physical interaction with the display device 21, e.g., by contacting the display panel of the display device 21 with a stylus or fingertip. A user interface element (e.g., 23, 24 and/or 25 shown in FIG. 1) may have a corresponding active region, such that, by touching the display panel within the active region associated with the user interface element, an input associated with the user interface element is received by the user interface 50.

User interface 50 may additionally, or alternatively, include one or more controls 22 that may include without limitation a switch (e.g., pushbutton switch, toggle switch, slide switch) and/or a continuous actuator (e.g., rotary or linear potentiometer, rotary or linear encoder). In an embodiment, a control 22 has a dedicated function, e.g., display contrast, power on/off, and the like. Control 22 may also have a function that may vary in accordance with an operational mode of the electrosurgical system 100. A user interface element (e.g., 23 shown in FIG. 1) may be provided to indicate the function of the control 22. Control 22 may also include an indicator, such as an illuminated indicator, e.g., a single- or variably-colored LED (light emitting diode) indicator.

In some embodiments, the electrosurgical power generating source 16 is configured to provide microwave energy at an operational frequency from about 300 MHz to about 2500 MHz. In other embodiments, the power generating source 16 is configured to provide microwave energy at an operational frequency from about 300 MHz to about 10 GHz. Power generating source 16 may be configured to provide various frequencies of electromagnetic energy.

Feedlines 1a, 2a and 3a may be formed from a suitable flexible, semi-rigid or rigid microwave conductive cable, and may connect directly to an electrosurgical power generating source 16. Feedlines 1a, 2a and 3a may have a variable length from a proximal end of the radiating sections "R1", "R2" and "R3", respectively, to a distal end of the transmission lines 10, 11 and 12, respectively, ranging from a length of about one inch to about twelve inches. Feedlines 1a, 2a and 3a may be made of stainless steel, which generally offers the strength required to puncture tissue and/or skin. Feedlines 1a, 2a and 3a may include an inner conductor, a dielectric material coaxially surrounding the inner conductor, and an outer conductor coaxially surrounding the dielectric material. Radiating sections "R1", "R2" and "R3" may be formed from a portion of the inner conductor that extends distal of the feedlines 1a, 2a and 3a, respectively, into the radiating sections "R1", "R2" and "R3", respectively. Feedlines 1a, 2a and 3a may be cooled by fluid, e.g., saline, water or other suitable coolant fluid, to improve power handling, and may include a stainless steel catheter. Transmission lines 10, 11 and 12 may additionally, or alternatively, provide a conduit (not shown) configured to provide coolant fluid from a coolant source 32 to the energy applicator array "E".

As shown in FIG. 1, the electrosurgical system 100 may include a reference electrode 19 (also referred to herein as a "return" electrode). Return electrode 19 may be electrically coupled via a transmission line 20 to the power generating source 16. During a procedure, the return electrode 19 may be positioned in contact with the skin of the patient or a surface of the organ "OR". When the surgeon activates the energy applicator array "E", the return electrode 19 and the transmission line 20 may serve as a return current path for the current flowing from the power generating source 16 through the probes 1, 2 and 3.

During microwave ablation, e.g., using the electrosurgical system 100, the energy applicator array "E" is inserted into or placed adjacent to tissue and microwave energy is supplied thereto. Ultrasound or computed tomography (CT) guidance may be used to accurately guide the energy applicator array "E" into the area of tissue to be treated. Probes 1, 2 and 3 may be placed percutaneously or surgically, e.g., using conventional surgical techniques by surgical staff. A clinician may pre-determine the length of time that microwave energy is to be applied. Application duration may depend on a variety of factors such as energy applicator design, number of energy applicators used simultaneously, tumor size and location, and whether the tumor was a secondary or primary cancer. The duration of microwave energy application using the energy applicator array "E" may depend on the progress of the heat distribution within the tissue area that is to be destroyed and/or the surrounding tissue.

FIG. 1 shows a targeted region including ablation targeted tissue represented in sectional view by the solid line "T". It may be desirable to ablate the targeted region "T" by fully engulfing the targeted region "T" in a volume of lethal heat elevation. Targeted region "T" may be, for example, a tumor that has been detected by a medical imaging system 30.

Medical imaging system 30, according to various embodiments, includes a scanner (e.g., 15 shown in FIG. 1) of any suitable imaging modality, or other image acquisition device capable of generating input pixel data representative of an image, e.g., a digital camera or digital video recorder. Medical imaging system 30 may additionally, or alternatively, include a medical imager operable to form a visible representation of the image based on the input pixel data. Medical imaging system 30 may include a storage device such as an internal memory unit, which may include an internal memory card and removable memory. In some embodiments, the medical imaging system 30 may be a multi-modal imaging system capable of scanning using different modalities. Examples of imaging modalities that may be suitably and selectively used include X-ray systems, ultrasound (UT) systems, magnetic resonance imaging (MRI) systems, computed tomography (CT) systems, single photon emission computed tomography (SPECT), and positron emission tomography (PET) systems. Medical imaging system 30, according to embodiments of the present disclosure, may include any device capable of generating digital data representing an anatomical region of interest. Medical imaging system 30 may be a multi-modal imaging system capable of scanning tissue in a first modality to obtain first modality data and a second modality to obtain second modality data, wherein the first modality data and/or the second modality data includes tissue temperature information. The tissue temperature information acquired by the one or more imaging modalities may be determined by any suitable method, e.g., calculated from density changes within the tissue.

Image data representative of one or more images may be communicated between the medical imaging system 30 and a processor unit 26. Medical imaging system 30 and the processor unit 26 may utilize wired communication and/or wireless communication. Processor unit 26 may include any type of computing device, computational circuit, or any type of processor or processing circuit capable of executing a series of instructions that are stored in a memory (not shown) associated with the processor unit 26. Processor unit 26 may be adapted to run an operating system platform and application programs. Processor unit 26 may receive user inputs from a keyboard (not shown), a pointing device 27, e.g., a mouse, joystick or trackball, and/or other device communicatively coupled to the processor unit 26.

A scanner (e.g., 15 shown in FIG. 1) of any suitable imaging modality may additionally, or alternatively, be disposed in contact with the organ "OR" to provide image data. As an illustrative example, the two dashed lines 15A in FIG. 1 bound a region for examination by the scanner 15, e.g., a real-time ultrasonic scanner.

In FIG. 1, the dashed line 8 surrounding the targeted region "T" represents the ablation isotherm in a sectional view through the organ "OR". Such an ablation isotherm may be that of the surface achieving possible temperatures of approximately 50° C. or greater. The shape and size of the ablation isotherm volume, as illustrated by the dashed line 8, may be influenced by a variety of factors including the configuration of the energy applicator array "E", the geometry of the radiating sections "R1", "R2" and "R3", cooling of the probes 1, 2 and 3, ablation time and wattage, and tissue characteristics. Processor unit 26 may be connected to one or more display devices (e.g., 21 shown in FIG. 1) for displaying output from the processor unit 26, which may be used by the clinician to visualize the targeted region "T" and/or the ablation isotherm volume 8 in real-time or near real-time during a procedure, e.g., an ablation procedure.

In embodiments, real-time data and/or near real-time data acquired from CT scan, ultrasound, or MRI (or other scanning modality) that includes tissue temperature information may be outputted from the processor unit 26 to one or more display devices. Processor unit 26 is adapted to analyze image data including tissue temperature information to determine a specific absorption rate (SAR) around an energy applicator as a function of the tissue temperature information obtained from the image data. A possible advantage to taking SAR directly from the patient is that any tissue inconsistencies in the local area of the antenna or electrode would be detected using this SAR. Calculating SAR from the electrode or antenna as it is being used in the patient may allow detection of the beginning of a non-uniform ablation field.

In some embodiments, the patient's anatomy may be scanned by one or more of several scanning modalities, such as CT scanning, MRI scanning, ultrasound, PET scanning, etc., so as to visualize the tumor and the surrounding normal tissue. The tumor dimensions may thereby be determined and/or the location of the tumor relative to critical structures and the external anatomy may be ascertained. An optimal number and size of energy applicators might be selected so that the ablation isotherms can optimally engulf and kill the tumor with a minimal number of electrode insertions and minimal damage to surrounding healthy tissue.

Electrosurgical system 100 may include a library 200 including a plurality of thermal profiles or overlays $202\text{-}202_n$. As it is used in this description, "library" generally refers to any repository, databank, database, cache, storage unit and the like. Each of the overlays $202\text{-}202_n$ may include a thermal profile that is characteristic of and/or specific to a particular energy applicator design, particular energy applicator array, and/or exposure time. Examples of overlay embodiments are disclosed in commonly assigned U.S. patent application Ser. No. 11/520,171 filed on Sep. 13, 2006, entitled "PORTABLE THERMALLY PROFILING PHANTOM AND METHOD OF USING THE SAME", and U.S. patent application Ser. No. 11/879,061 filed on Jul. 16, 2007, entitled "SYSTEM AND METHOD FOR THERMALLY PROFILING RADIOFREQUENCY ELECTRODES", the disclosures of which are incorporated herein by reference in their entireties.

Library 200 according to embodiments of the present disclosure may include a database 284 that is configured to store and retrieve energy applicator data, e.g., parameters associated with one or more energy applicators (e.g., 1, 2 and 3 shown in FIG. 1) and/or one or more energy applicator arrays (e.g., "E" shown in FIG. 1). Parameters stored in the database 284 in connection with an energy applicator, or an energy applicator array, may include, but are not limited to, energy applicator (or energy applicator array) identifier, energy applicator (or energy applicator array) dimensions, a frequency, an ablation length (e.g., in relation to a radiating section length), an ablation diameter, a temporal coefficient, a shape metric, and/or a frequency metric. In an embodiment, ablation pattern topology may be included in the database 284, e.g., a wireframe model of an energy applicator array (e.g., 25 shown in FIG. 1) and/or a representation of a radiation pattern associated therewith.

Library 200 according to embodiments of the present disclosure may be in communicatively associated with a picture archiving and communication system (PACS) database (shown generally as 58 in FIG. 1), e.g., containing DICOM (acronym for Digital Imaging and Communications in Medicine) formatted medical images. PACS database 58 may be configured to store and retrieve image data including tissue temperature information. As shown in FIG. 1, the processor unit 26 may be communicatively associated with the PACS database 58. It is envisioned and within the scope of the present disclosure that image data associated with a prior treatment of a target tissue volume may be retrieved from the PACS database 58 and the SAR may be calculated as a function of the tissue temperature information from the image data.

Images and/or non-graphical data stored in the library 200, and/or retrievable from the PACS database 58, may be used to configure the electrosurgical system 100 and/or control operations thereof. For example, thermal profiling data associated with an energy applicator, according to embodiments of the present disclosure, may be used as a feedback tool to control an instrument's and/or clinician's motion, e.g., to allow clinicians to avoid ablating critical structures, such as large vessels, healthy organs or vital membrane barriers.

Figure 20:
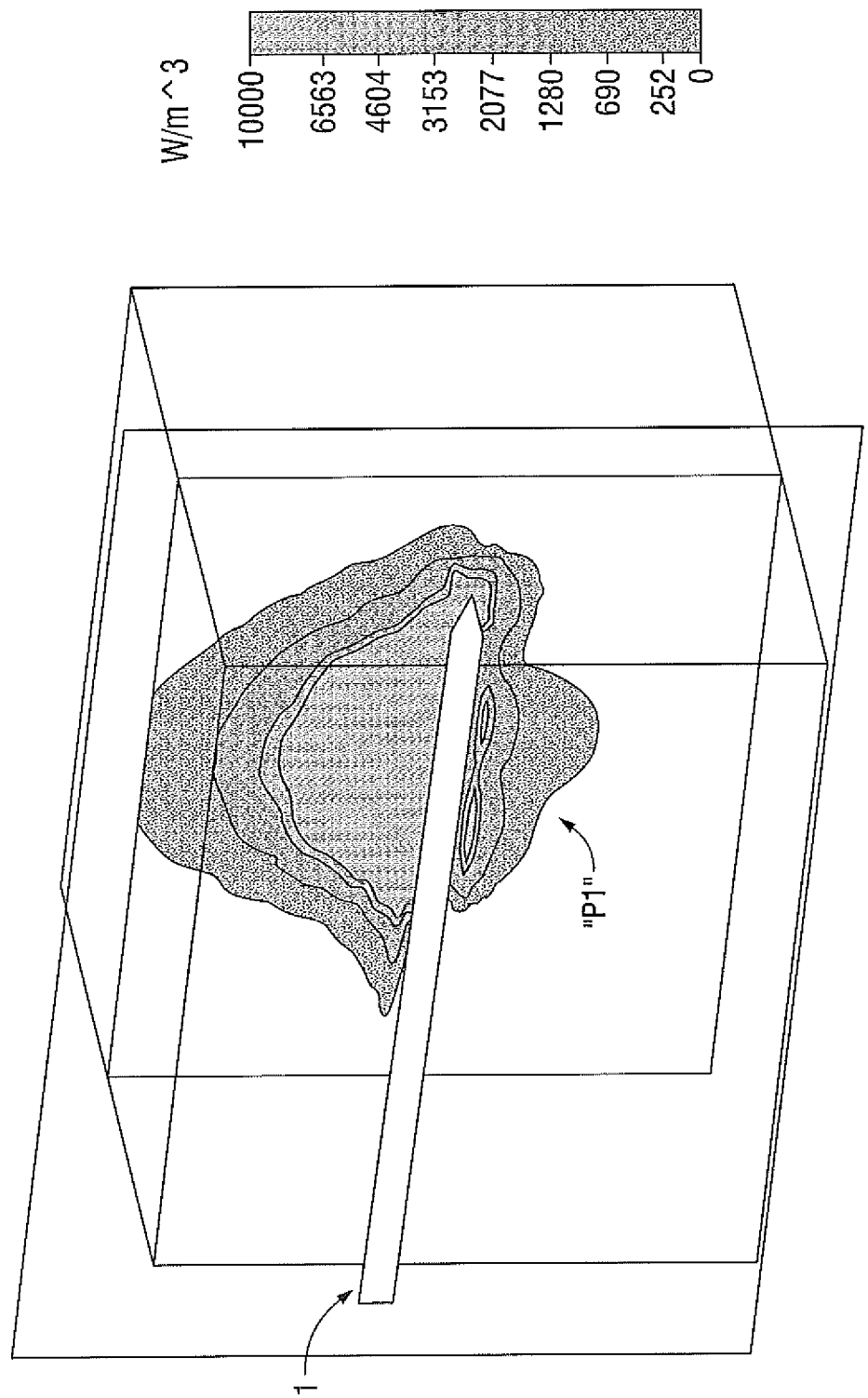
FIG. 20 is a diagrammatic representation of a simulated radiation pattern for an energy applicator according to an embodiment of the present disclosure.
Figure 21:
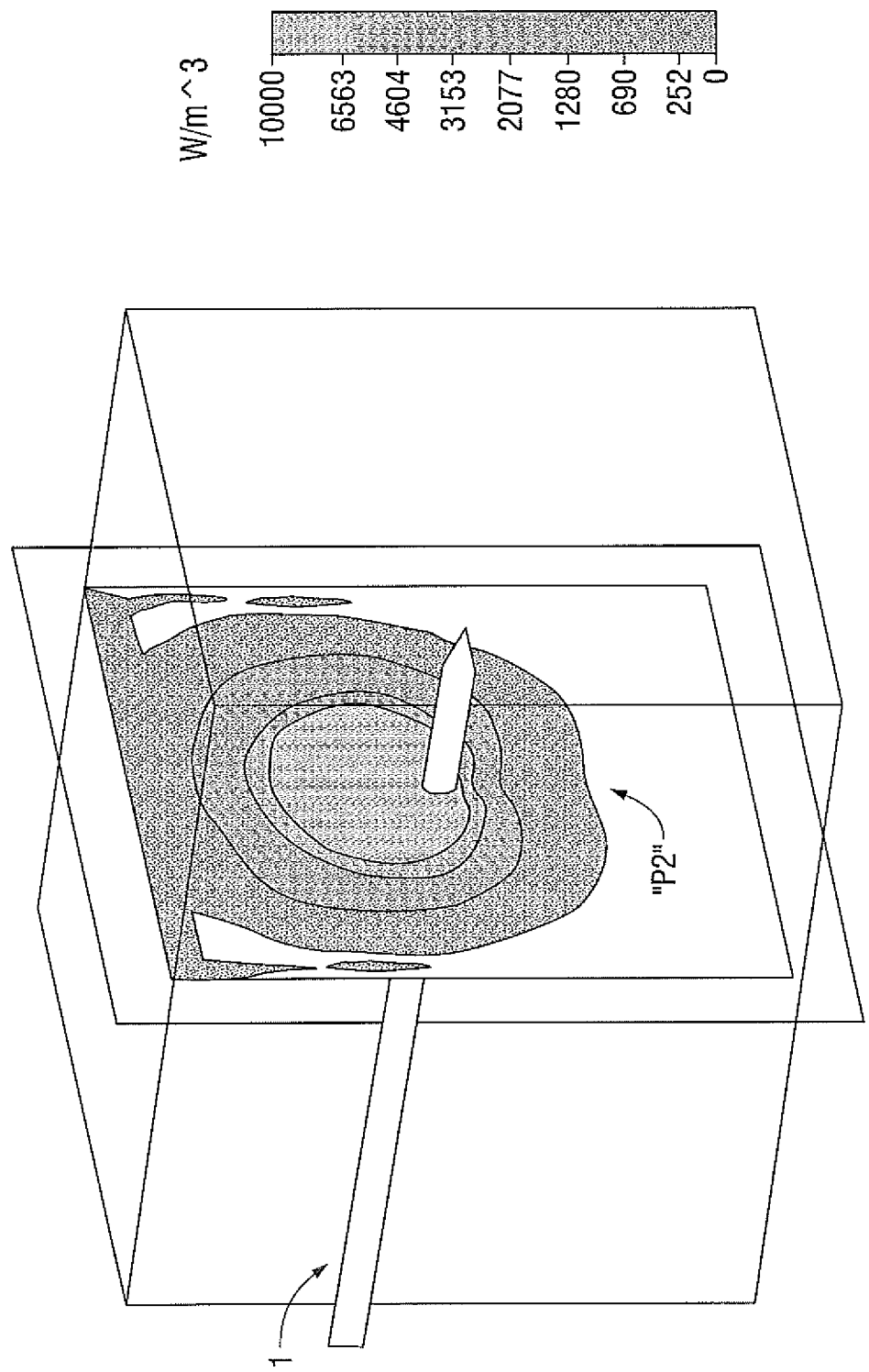
FIG. 21 is a diagrammatic representation of a simulated radiation pattern for an energy applicator according to another embodiment of the present disclosure.

Images and/or non-graphical data stored in the library 200, and/or retrievable from the PACS database 58, may be used to facilitate planning and effective execution of a procedure, e.g., an ablation procedure. Thermal profile data associated with an energy applicator, according to embodiments of the present disclosure, may be used as a predictive display of how an ablation will occur prior to the process of ablating. Thermal profile data associated with an energy applicator, according to embodiments of the present disclosure, may be used to determine a specific absorption rate (SAR) around the energy applicator. A simulated radiation pattern for the energy applicator may be generated as a function of the SAR around the energy applicator. For example, the Pennes' bio-heat equation coupled with electrical field equations in a finite element analysis (FEA) environment generally provides a governing structure for computer simulations modeling energy deposition in biological tissues. It is envisioned and within the scope of the present disclosure that the Pennes' bio-heat equation coupled with electrical field equations in a FEA environment may be used to generate simulated radiation patterns for an energy applicator as a function of the SAR around the energy applicator. Images, simulated radiation patterns (e.g., "P1" and "P2" shown in FIGS. 20 and 21, respectively) and/or information displayed on the display device 21 of the user interface 50, for example, may be used by the clinician to better visualize and understand how to achieve more optimized results during thermal treatment of tissue, such as, for example, ablation of tissue, tumors and cancer cells.

Figure 2:
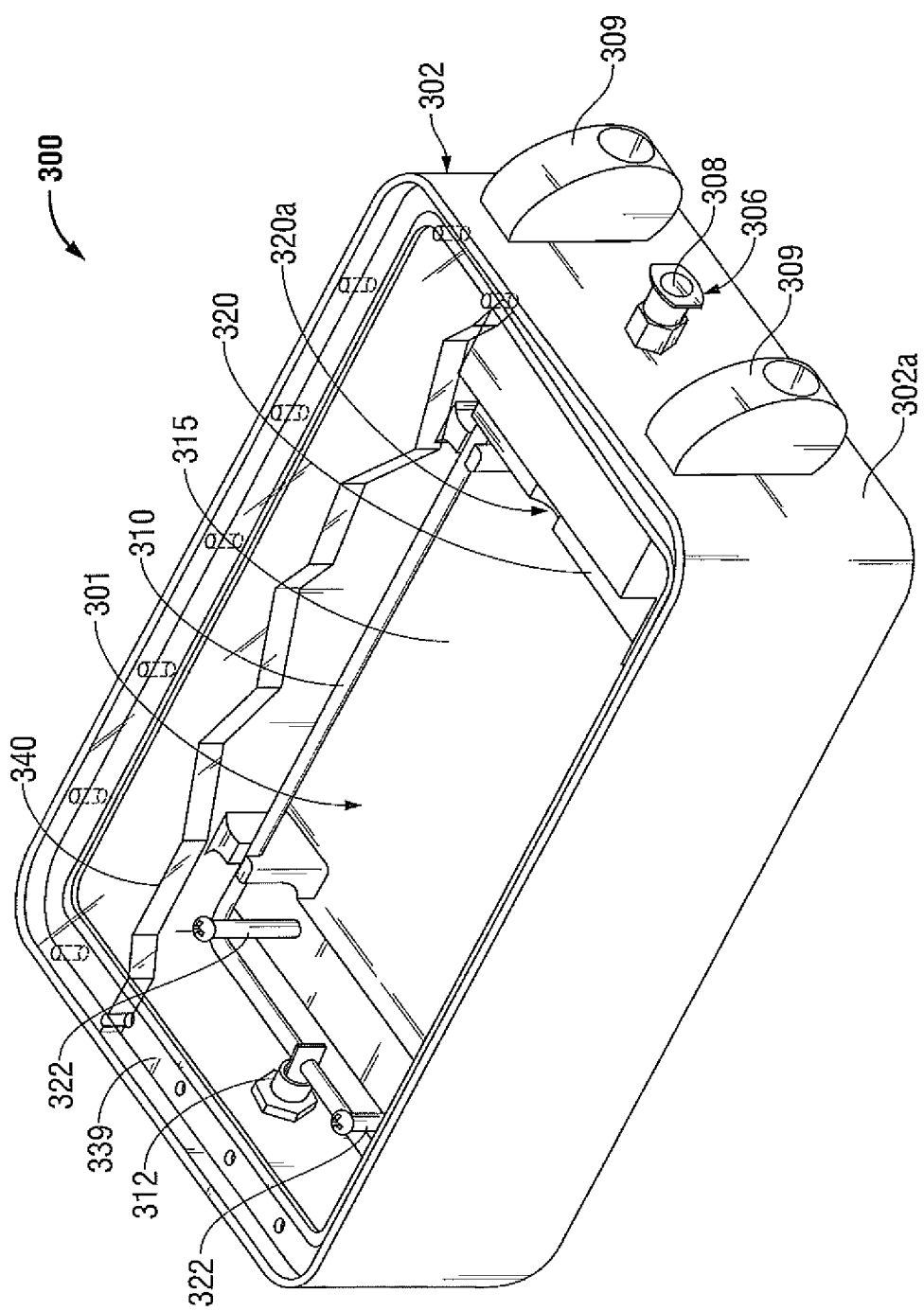
FIG. 2 is a perspective view, partially broken-away, of an embodiment of a test fixture assembly in accordance with the present disclosure.
Figure 3:
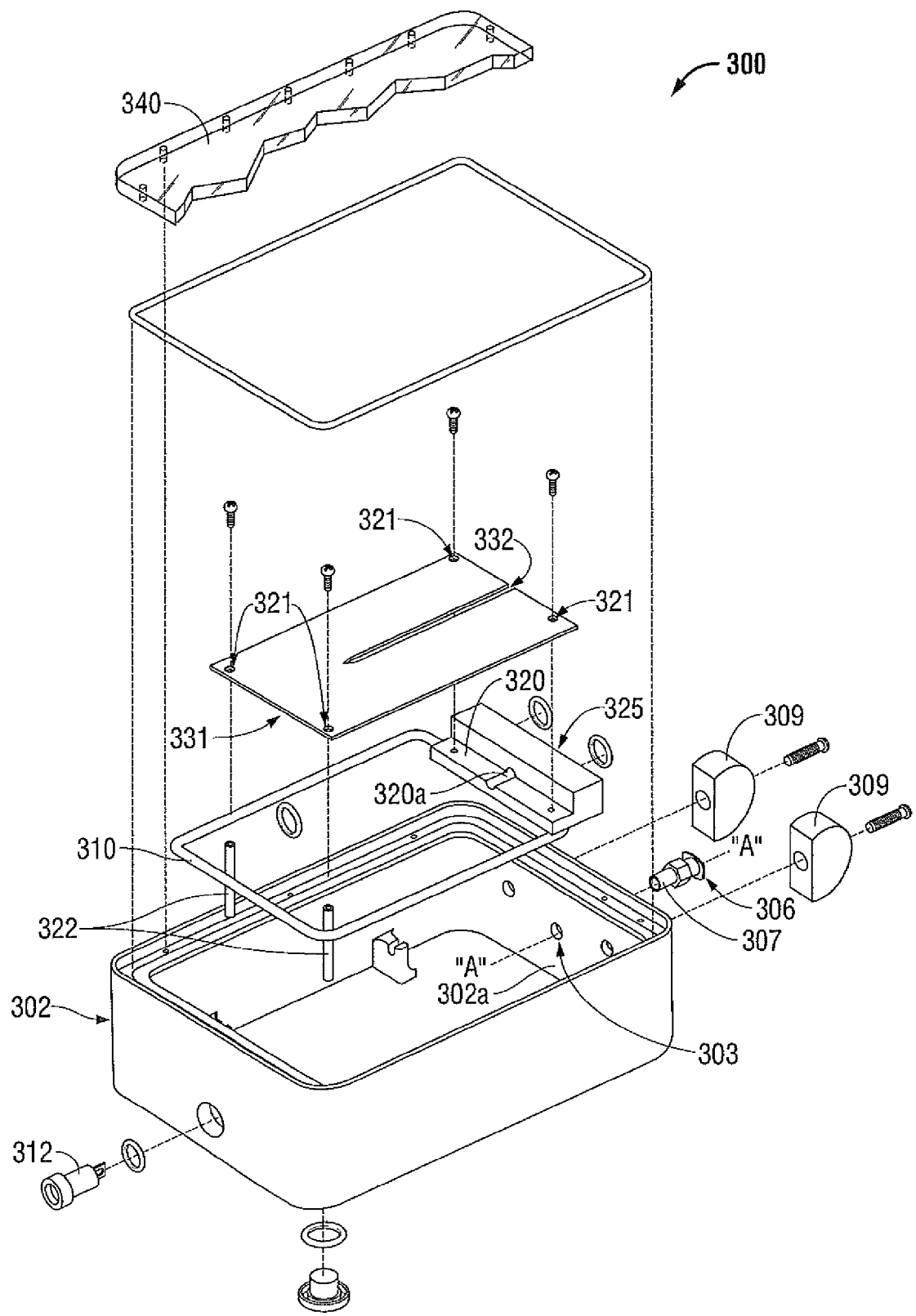
FIG. 3 is an exploded, perspective view, partially broken-away, of the test fixture assembly of FIG. 2 shown with a thermally-sensitive medium according to an embodiment of the present disclosure.
Figure 4:
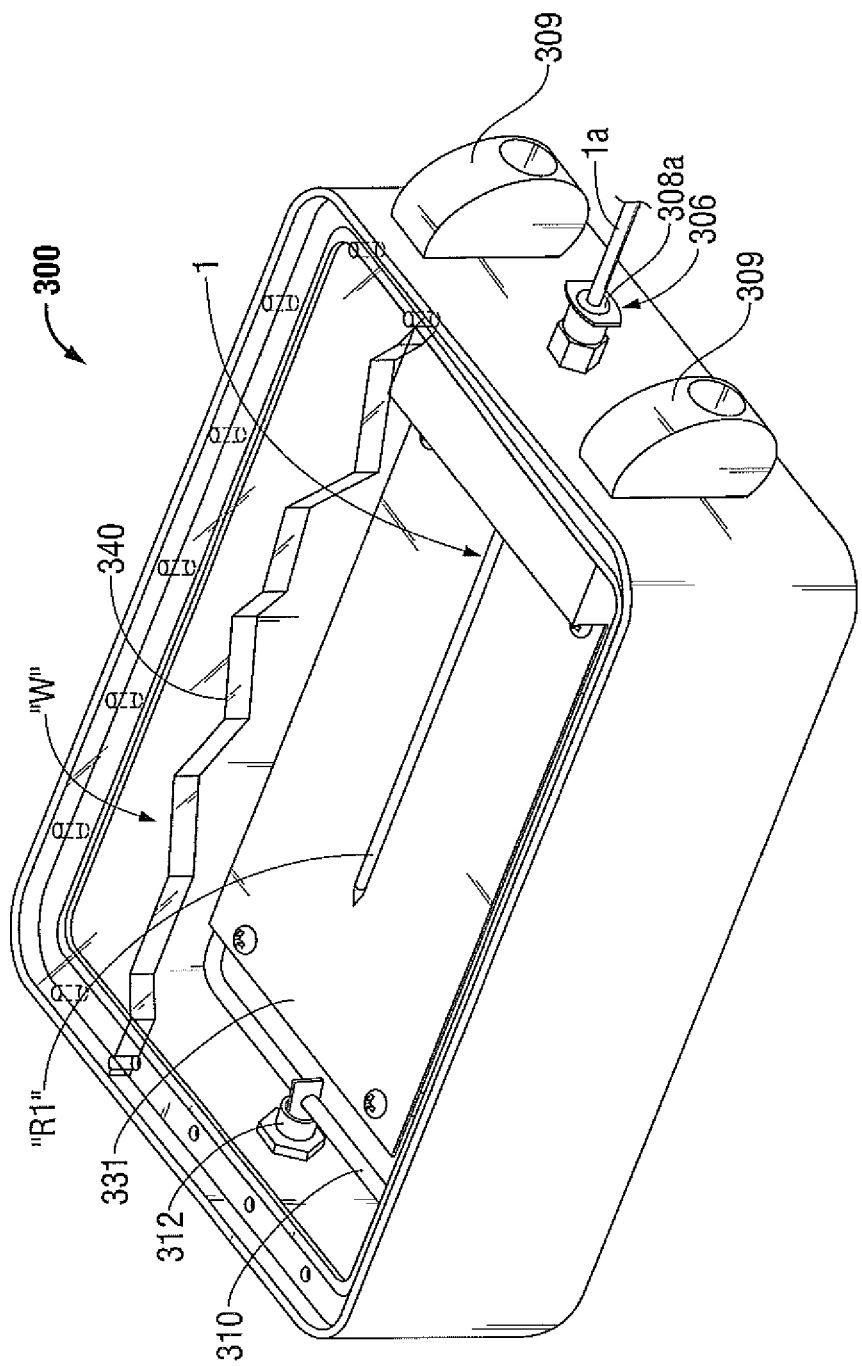
FIG. 4 is a perspective view, partially broken-away, of test fixture assembly of FIGS. 2 and 3 according to an embodiment of the present disclosure shown with an energy applicator associated therewith.

An embodiment of a system (shown generally as 900 in FIG. 9) suitable for specific absorption rate measurement and characterization of energy-delivery devices in accordance with the present disclosure includes the test fixture assembly 300 of FIGS. 2 through 4, a thermally-sensitive, color-changing medium (e.g., 331 shown in FIGS. 3 and 4) disposed within the test fixture assembly 300, and may include a hydrogel material 304 disposed around the thermally-sensitive medium. Test fixture assembly 300 includes a housing 302 including a wall 302a, a port 303 defined in the wall 302a, and a support member 325 adapted to support at least a portion of a thermally-sensitive, color-changing medium disposed within an interior area (shown generally as 301 in FIG. 2) of the housing 302. The thermally-sensitive, color-changing medium may be a sheet or layer of thermally-sensitive paper or film, may have a single- or multi-layer structure, and may include a supporting substrate. A layer of a thermally-sensitive medium may be composed of different materials.

Housing 302 may be configured to contain a quantity of a fluid and/or gel material 304, e.g., an electrically and thermally conductive polymer, hydrogel, or other suitable transparent or substantially-transparent medium having electrical and thermal conductivity. Housing 302 includes a bottom portion 315 and a wall 302a extending upwardly from the bottom portion 315 to define an interior area or space (e.g., 301 shown in FIG. 2). Housing 302 may be fabricated from any suitable material, e.g., plastic or other moldable material, and may have a substantially rectangular or box-like shape. In embodiments, the housing 302 may include an electrically non-conductive material, e.g., plastics, such as polyethylene, polycarbonate, polyvinyl chloride (PVC), or the like. Housing 302 may be fabricated from metals, plastics, ceramics, composites, e.g., plastic-metal or ceramic-metal composites, or other materials. In some embodiments, the housing 302 is formed of a high thermal conductivity material, e.g., aluminum. The shape and size of the housing 302 may be varied from the configuration depicted in FIGS. 2 through 4. Housing 302 may have the different anatomical shapes, such as, for example, circular, ovular, kidney-shaped, liver-shaped, or lung shaped, which may allow a clinician to better visualize the potential effects of thermal treatment on a patient prior to actually performing the treatment procedure.

Housing 302, according to embodiments of the present disclosure, includes one or more ports (e.g., 303 shown in FIG. 3) defined in the housing 302 and configured to allow at least a distal portion of a probe (shown generally as 1 in FIGS. 1, 4, 7, 8 and 9) to be disposed in an interior area of the housing 302. The port(s) may be configured to accommodate different size probes.

As shown in FIG. 3, a fixture or fitting 306 may be provided to the port 303. Fitting 306 may be configured to extend through a wall 302a of the housing 302. Fitting 306 generally includes a tubular portion (e.g., 307 shown in FIG. 3) defining a passageway (e.g., 308 shown in FIG. 2) configured to selectively receive a probe (e.g., 1 shown in FIG. 4) therethrough. In embodiments, the fitting 306 may be configured to inhibit leakage of the hydrogel 304 from within the housing 302, e.g., when the probe is removed from the fitting 306. Fitting 306 may additionally, or alternatively, form a substantially fluid tight seal around the probe when the probe is inserted therethrough. Fitting 306 may be a single-use fitting. Fitting 306 may be replaceable after each use or after several uses. Fitting 306 may include, but is not limited to, a luer-type fitting, a pierceable membrane port, and the like. Guards 309 may be disposed on opposite sides of the fitting 306 to prevent inadvertent contact or disruption of the fitting 306. Test fixture assembly 300, according to embodiments of the present disclosure, may include a plurality of ports defined in the housing 302, e.g., to accommodate multiple probes. Test fixture assembly 300 may additionally, or alternatively, include a plurality of fittings 306.

In some embodiments, the test fixture assembly 300 includes a ground ring 310 disposed within the housing 302. Ground ring 310 may include any suitable electrically-conductive material, e.g., metal such as aluminum. During operation of the thermal profiling system 900, the ground ring 310 may receive and/or transmit electromagnetic energy from/to an energy applicator associated with the test fixture assembly 300. As shown in FIGS. 2 and 3, the ground ring 310 may have a shape that substantially complements the shape of the housing 302, e.g., to extend substantially around an inner perimeter of the housing 302. A ground connection 312 may be provided that is adapted to electrically connect to the ground ring 310. As shown in FIGS. 3 and 4, the ground connection 312 may extend through a wall of the housing 302, and may be used to electrically connect the ground ring 310 to an electrosurgical power generating source (e.g., 916 shown in FIG. 9). In some embodiments, the ground ring 310 may be removable. The ground ring 310 may be removed in order to reduce any reflected energy that may be caused by the presence of the ground ring 310, which may be influenced by probe configuration and operational parameters. For example, it may be desirable to remove the ground ring 310 when microwave operational frequencies are used.

Figure 6:
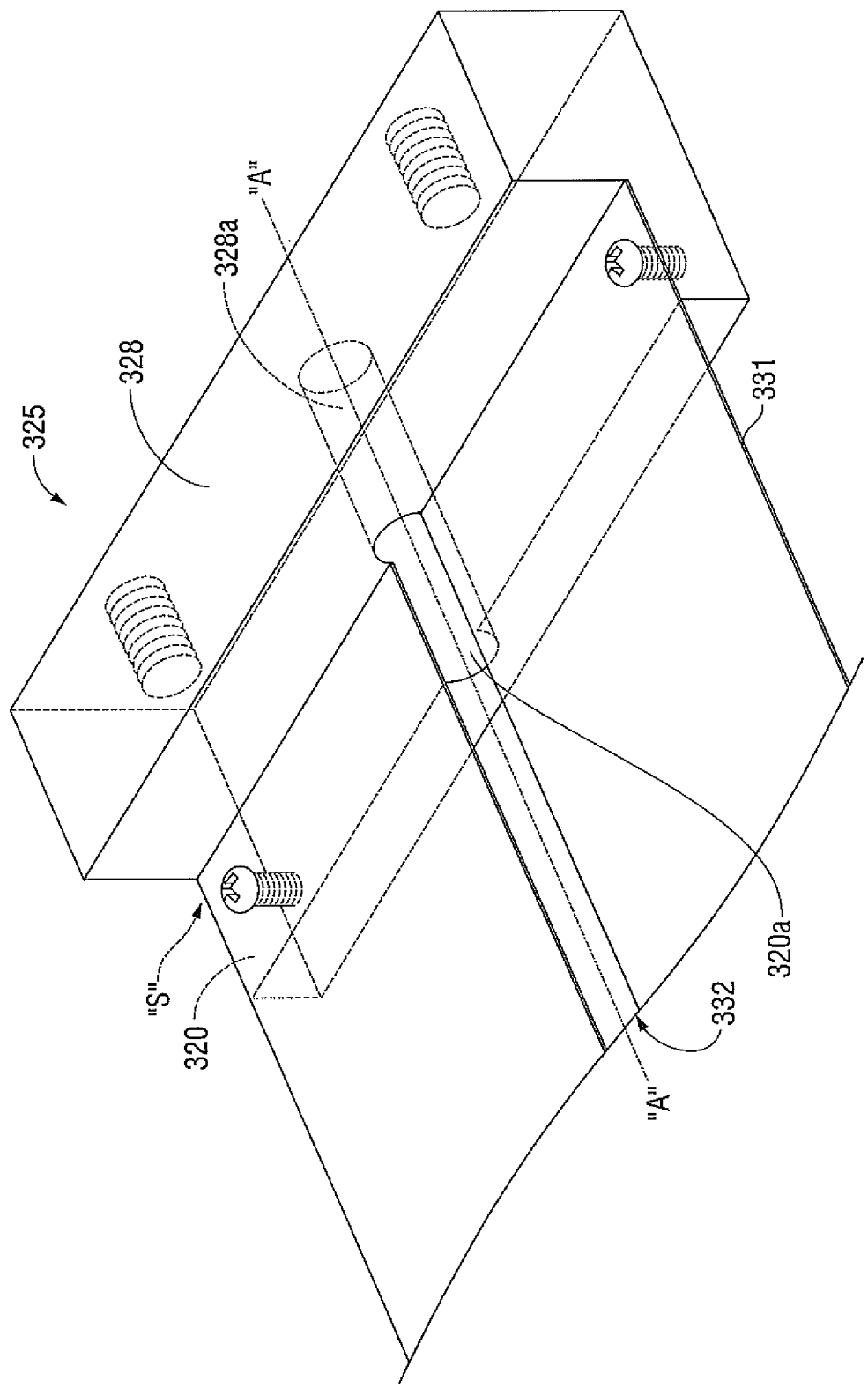
FIG. 6 is a perspective view of a support member of the test fixture assembly of FIGS. 2 through 4 according to an embodiment of the present disclosure shown with a portion of the thermally-sensitive medium of FIG. 5 associated therewith.

Test fixture assembly 300 according to embodiments of the present disclosure includes a support member 325 disposed on and extending inwardly from an inner surface of a wall 302a of the housing 302, and may include at least one support rod 322 extending upwardly into the housing 302 from a lower surface thereof. FIG. 6 shows an embodiment of the support member 325 that includes a shelf portion 320, a recess in the form of a groove 320a defined in the planar top surface "S" of the shelf portion 320, and a shelf support member 328 coupled to the shelf portion 320. Shelf portion 320 and the shelf support member 328 may be integrally formed. As shown in FIG. 6, a channel 328a is defined in the shelf support member 328 and extends therethrough. In some embodiments, the channel 328a has a substantially cylindrical shape and the groove 320a has a substantially half-cylindrical shape, and the groove 320a may be substantially aligned with a lower, half-cylindrical portion of the channel 328a.

Figure 9:
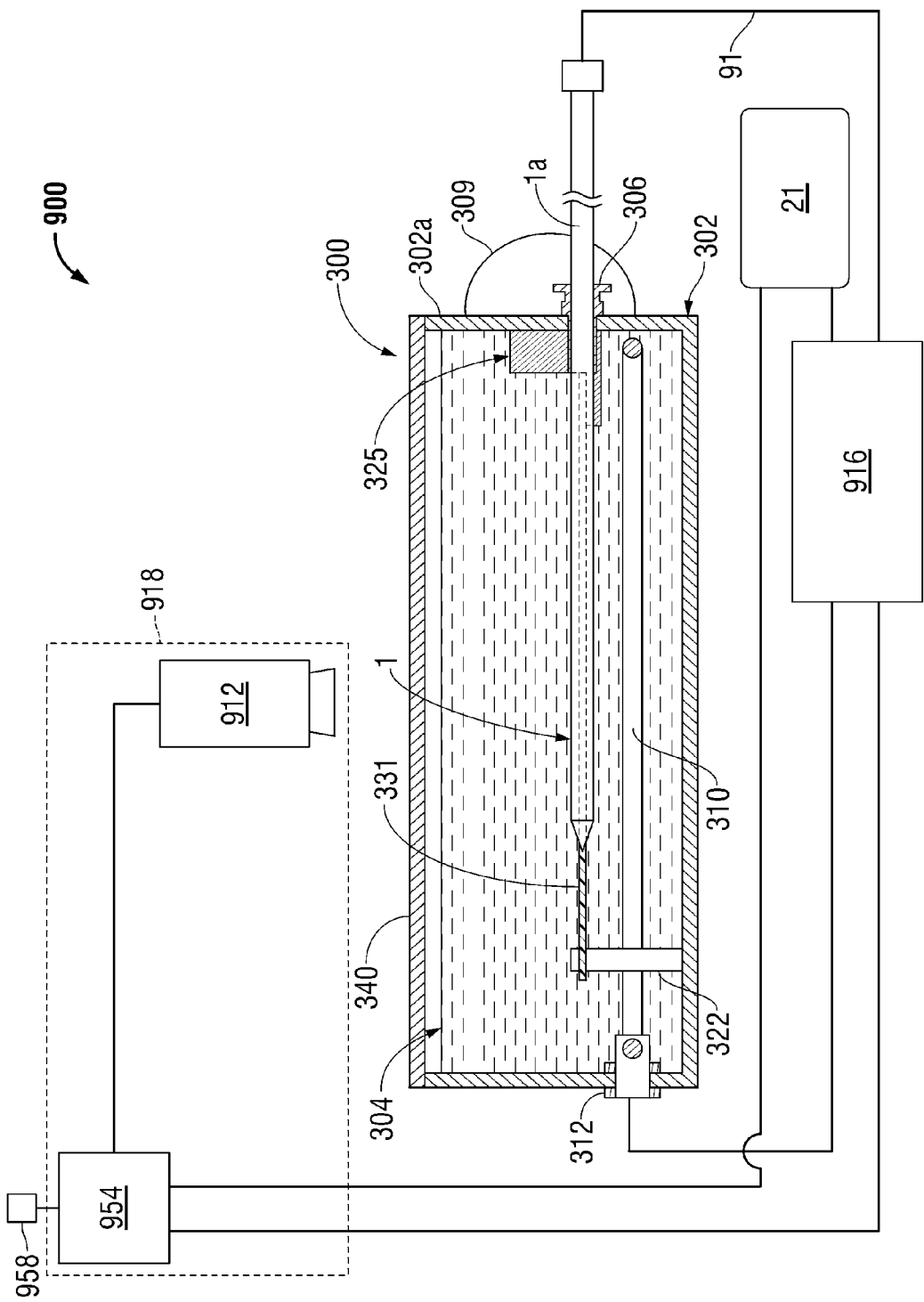
FIG. 9 is a schematic, longitudinal cross-sectional view of an embodiment of a thermal profiling system including the test fixture assembly of FIGS. 2 through 4 and the energy applicator and the thermally-sensitive medium of FIGS. 7 and 8 in accordance with the present disclosure.

FIG. 9 shows an embodiment of a thermal profiling system 900 according to the present disclosure that includes the test fixture assembly 300 of FIGS. 2 through 4 and an imaging system 918. Imaging system 918 includes an image acquisition unit 912 capable of generating image data, and may include an image processing unit 954 in communication with the image acquisition unit 912. Image acquisition unit 912 may include any suitable device capable of generating input pixel data representative of an image, e.g., a digital camera or digital video recorder. An image may have 5120 scan lines, 4096 pixels per scan lines and eight bits per pixel, for example. As described in more detail herein, at least one sheet or layer of a suitable thermally-sensitive medium 331 is disposed within an interior area (shown generally as 301 in FIG. 2) of the housing 302. Image acquisition unit 912, according to embodiments to the present disclosure, is configured to capture time-series image data of thermal radiation patterns formed on the thermally-sensitive medium 331, and may be disposed over the interior area of the housing 302 or otherwise suitably positioned to facilitate image capture of the thermally-sensitive medium 331, or portion thereof.

In some embodiments, the thermally-sensitive medium 331 may include liquid crystal (LC) thermometry paper. A plurality of sheets of the thermally-sensitive medium 331 may be provided to generate a set of thermal profiles thereon in accordance with characteristics of an energy applicator and/or parameters and/or settings of a power generating source. The shape, size and number of sheets of the thermally-sensitive medium 331 may be varied from the configuration depicted in FIGS. 3 and 4. In some embodiments, the thermally-sensitive medium 331 may have a shape that conforms to the shape of the selected housing (e.g., 302 shown in FIGS. 2 through 4) and/or the thermally-sensitive medium 331 may be shaped to allow circulation of a heated medium, e.g., hydrogel, thereabout.

Thermal profiling system 900 may include an electrosurgical power generating source 916. As shown in FIG. 9, the feedline 1a of the energy applicator 1 associated with the test fixture assembly 300 may be electrically coupled to an active port or terminal of the electrosurgical power generating source 916, and the ground connection 321 of the test fixture assembly 300 may be electrically coupled to a return port or terminal of the power generating source 916.

Thermal profiling system 900, according to embodiments of the present disclosure, may include a temperature control unit (not shown) capable of detecting the temperature of the hydrogel 304 and maintaining the hydrogel 304 at a predetermined temperature or temperature range. In accordance with embodiments of the present disclosure, the difference between the ambient temperature of the hydrogel 304 and the threshold temperature of the thermally-sensitive medium 331 is designed to be relatively small, e.g., to allow close to adiabatic conditions. For example, the thermal profiling system 900 may be configured to maintain the hydrogel 304 at a temperature of about 34.5° C., and the thermally-sensitive medium 331 may be selected to have a threshold temperature of about 35.0° C.

Figure 5:
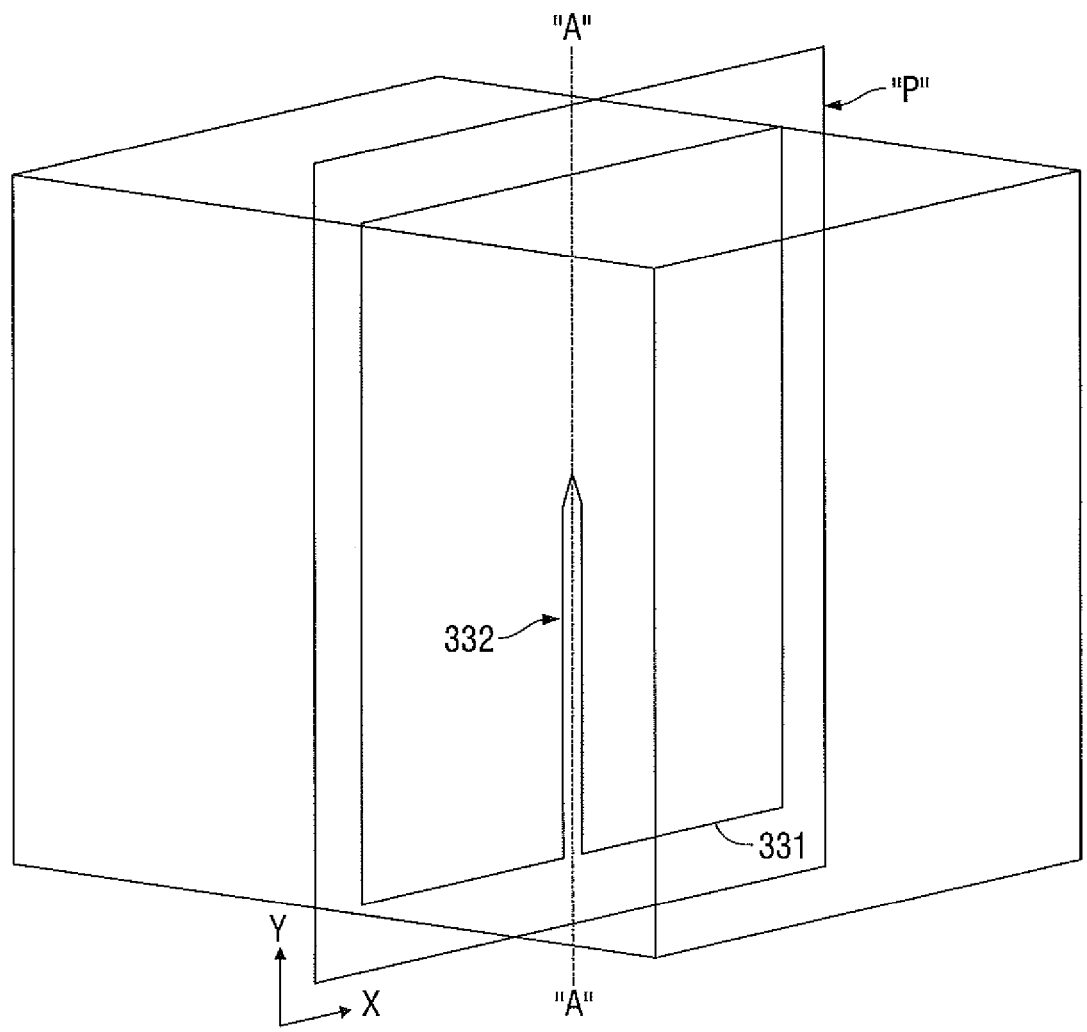
FIG. 5 is a cross-sectional view of an embodiment of a thermally-sensitive medium including a cut-out portion in accordance with the present disclosure.

Thermally-sensitive medium 331 according to embodiments of the present disclosure includes a cut-out portion (e.g., 332 shown in FIG. 5) defining a void in the thermally-sensitive medium 331. The cut-out portion may be configured to substantially match the profile of an energy applicator, and may be configured to provide a gap (e.g., "G" shown in FIG. 7) between the energy applicator and the thermally-sensitive medium 331 at the edge of the cut-out portion. Thermally-sensitive medium 331 may have any suitable thermal sensitivity. In some embodiments, the thermally-sensitive medium 331 has a thermal sensitivity of about one degree Celsius. Thermally-sensitive medium 331, or portion thereof, may be disposed over at least a portion of the support member 325. Additionally, or alternatively, at least a portion of the thermally-sensitive medium 331 may be disposed over one or more support rods 322.

In some embodiments, at least a portion of the thermally-sensitive medium 331 is disposed over the shelf portion 320 and positioned to substantially align a longitudinal axis (e.g., "A-A" shown in FIG. 5) of a cut-out portion 332 with a central longitudinal axis (e.g., "A-A" shown in FIG. 6) of the channel 328a of the shelf support member 328. In some embodiments, a longitudinal axis (e.g., "A-A" shown in FIG. 5) of the cut-out portion 332 is arranged parallel to the central longitudinal axis (e.g., "A-A" shown in FIG. 6) of the channel 328a. As cooperatively shown in FIGS. 3 and 9, a fitting 306 may be provided to the port 303 defined in the wall 302a of the housing 302, wherein a tubular portion 307 of the fitting 306 may be configured to extend through the port 303 and into the channel 328a of the support member 325. Tubular portion 307 disposed within the port 303 and channel 328a may help to maintain alignment of the energy applicator (e.g., 1 shown in FIGS. 4 and 9) with respect to the cut-out portion 332 of the thermally-sensitive medium 331. Fitting 307 may be provided with a sleeve member (e.g., 308a shown in FIG. 4) substantially coaxially aligned with the tubular portion 307, e.g., to provide a resiliently compressible seal around an energy applicator portion disposed therein. The sleeve member may be formed of a compliant material, e.g., silicon, natural or synthetic rubber, or other suitable resiliently compressible material.

In some embodiments, the shelf portion 320 and one or more support rods 322 function to support a thermally-sensitive medium 331 within the housing 302. Shelf portion 320 and the support rod(s) 322, according to embodiments of the present disclosure, may be configured to support the thermally-sensitive medium 331 such that the thermally-sensitive medium 331 is maintained in a plane (e.g., "P" shown in FIG. 5) substantially parallel to a facing surface of the bottom portion 315 of the housing 302. Shelf portion 320 and the support rod(s) 322 may additionally, or alternatively, be configured to support the thermally-sensitive medium 331 such that the thermally-sensitive medium 331 is maintained in a plane substantially parallel to a plane of the shelf portion 320. Shelf portion 320 and the support rod(s) 322 may additionally, or alternatively, be configured to support the thermally-sensitive medium 331 such that a longitudinal axis (e.g., "A-A" shown in FIG. 5) of the cut-out portion 332 is substantially aligned with the central longitudinal axis (e.g., "A-A" shown in FIG. 8) of an energy applicator (e.g., 1 shown in FIG. 8) associated therewith.

Thermal profiling system 900, according to embodiments of the present disclosure, includes a transparent housing portion (e.g., "W" shown in FIG. 4) for providing viewing into the interior area of the housing 302, and may include a cover 340 configured to selectively overlie the housing 302. Cover 340, or portion thereof, may be fabricated from any suitable transparent or substantially transparent material, e.g., glass, optically transparent thermoplastics, such as polyacrylic or polycarbonate. In some embodiments, the housing 302 includes a top edge portion (e.g., 339 shown in FIG. 2), which can take any suitable shape. Cover 340 may be releaseably securable to a top edge portion of the housing 302 by any suitable fastening element, e.g., screws, bolts, pins, clips, clamps, and hinges.

As shown in FIG. 9, the thermal profiling system 900 includes an imaging system 918 operatively associated with the electrosurgical power generating source 916 and the housing 302, and may include a display device 21 electrically coupled to the electrosurgical power generating source 916. For example, the imaging system 918 may include an image acquisition unit 912 for recording the visual changes occurring in thermally-sensitive medium 331 and/or parameters and/or settings of the electrosurgical power generating source 916 (e.g., power settings, time settings, wave settings, duty-cycle settings, energy applicator 1 configuration, etc.). Imaging system 918 may be communicatively coupled to a PACS database (e.g., 58 shown in FIG. 1). Imaging system 918 may also include an image processing unit 954 to which a portable storage medium 958 may be electrically connected. Portable storage medium 958 may, among other things, allow for transfer of image data in DICOM format to a PACS database (e.g., 58 shown in FIG. 1). As shown in FIG. 9, the image processing unit 954 is electrically connected between the image acquisition unit 912 and the power generating source 916, and may be electrically connected to the display device 21.

Hereinafter, a method of measuring specific absorption rate and characterizing an energy applicator using a thermal phantom and image analysis in accordance with the present disclosure is described with reference to FIGS. 1 through 9. Test fixture assembly 300 of FIGS. 2 through 4 is provided, and a hydrogel material 304 is introduced into the interior area 301 of the housing 302 of the test fixture assembly 300. A thermally-sensitive medium 331 including a cut-out portion 332 is placed into the housing 302 containing hydrogel 304 therein, e.g., in such a manner that a color changing side of the thermally-sensitive medium 331 is facing the cover 340 or away from the bottom portion 315. Thermally-sensitive medium 331 may be positioned within the housing 302 such that at least a portion of thermally-sensitive medium 331 is placed on the shelf portion 320 of the support member 325 and/or at least a portion of thermally-sensitive medium 331 is placed on support rods 322. In one embodiment, fasteners, such as screws, may be used to secure the thermally-sensitive medium 331 to the shelf portion 320 and/or the support rods 322. With the thermally-sensitive medium 331 submerged in hydrogel 304 within the housing 302, the cover 340 may be secured to the housing 302, e.g., to substantially enclose the thermally-sensitive medium 331 within the housing 302.

Figure 7:
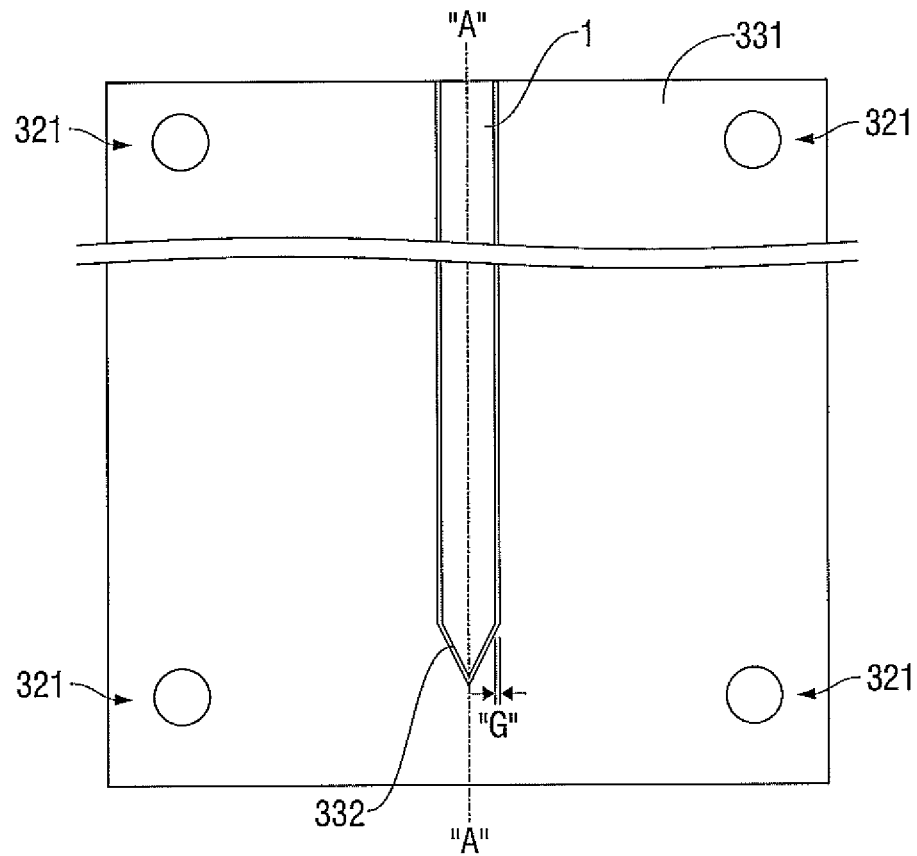
FIGS. 7 and 8 are partial, enlarged views schematically illustrating the thermally-sensitive medium of FIG. 5 and the energy applicator of FIG. 4 centrally aligned with the longitudinal axis of the thermally-sensitive medium's cut-out portion according to an embodiment of the present disclosure.

The selected energy applicator (e.g., 1 shown in FIGS. 1, 4 and 9) is introduced into the housing 302 through the port 303 by placing a distal tip portion (e.g., 1b shown in FIG. 1) into a fitting 306 disposed therein and advancing the energy applicator therethrough until at least a portion of the radiating section of the energy applicator is located with the cut-out portion 332 of the thermally-sensitive medium 331. As shown in FIG. 7, the energy applicator 1 disposed in the cut-out portion 332 may be spaced apart a distance or gap "G" from the thermally-sensitive medium 331. Gap "G" may be configured to be as narrow a distance as can be achieved, without making contact between the thermally-sensitive medium 331 and the energy applicator 1. In some embodiments, the gap "G" may be about 1 millimeter. As shown in FIG. 7, the width of the gap "G" may be substantially the same around the entire periphery of the energy applicator 1, e.g., to minimize errors in the image processing and analysis stage.

Energy applicator 1 is electrically connected to an active port or terminal of electrosurgical power generating source 916, and the ground connection 312 of the test fixture assembly 300 is electrically connected to a return port or terminal of power generating source 916. Test fixture assembly 300, according to embodiments of the present disclosure, is adapted to maintain the position of at least a distal portion of the energy applicator 1 disposed within the test fixture assembly 300 such that the central longitudinal axis (e.g., "A-A" shown in FIG. 8) of the energy applicator 1 is substantially parallel to a plane (e.g., "P" shown in FIG. 5) containing the thermally-sensitive medium 331.

In some embodiments, the power generating source 916 is configured or set to a predetermined setting. For example, power generating source 916 may be set to a predetermined temperature, such as a temperature that may be used for the treatment of pain (e.g., about 42° C. or about 80° C.), a predetermined waveform, a predetermined duty cycle, a predetermined time period or duration of activation, etc.

When the energy applicator 1 is positioned within the test fixture assembly 300, the imaging system 918 may be activated to record any visual changes in the thermally-sensitive medium 331, the settings and/or parameters of the power generating source 916, and the configuration of the energy applicator 1.

According to an embodiment of the present disclosure, prior to activation of the electrosurgical power generating source 916, a temperature of the hydrogel 304 within the housing 302 is stabilized to a temperature of approximately 37° C. When the power generating source 916 is activated, electromagnetic energy communicated between the radiating section (e.g., "R1" shown in FIG. 4) of the energy applicator 1 and ground ring 310 affects the thermally-sensitive medium 331 to create a thermal image (e.g., "S1" shown in FIG. 10) thereon.

Figures 12, 13:
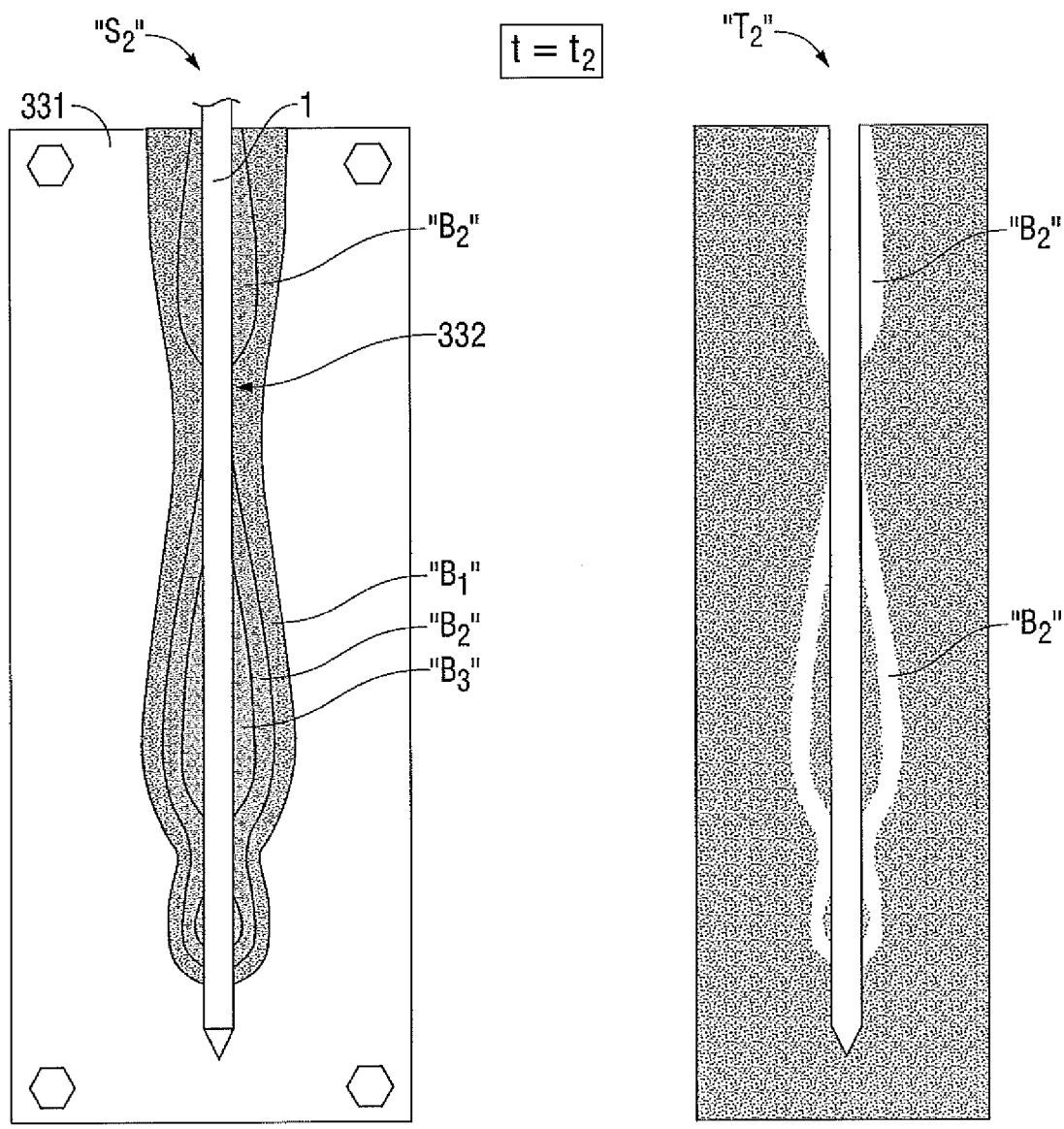
FIG. 12 is a schematic diagram illustrating the thermally-sensitive medium of the thermal profiling system of FIG. 9 during operation according to an embodiment of the present disclosure shown with a schematically-illustrated representation of a thermal radiation pattern formed on the thermally-sensitive medium at time t equal to $t_2$.
FIG. 13 is a schematic diagram illustrating a thresholded pattern image of a portion of the thermally-sensitive medium of FIG. 12 showing a selected temperature band captured at time t equal to $t_2$ according to an embodiment of the present disclosure.

The method may further include operating the imaging system 918 to capture a time series of thermal images (e.g., "S1", "S2" and "S3" shown in FIGS. 10, 12 and 14, respectively). For example, the temperature gradients or "halos" created on the thermally-sensitive medium 331 may be captured by the image acquisition unit 912 of the imaging system 918, and may be stored electronically in the image processing unit 954 or the portable storage medium 958 communicatively coupled thereto. As heat generated by the electromagnetic radiation emitted from energy applicator 1 affects the thermally-sensitive medium 331, the temperature gradients or "halos", e.g., colored rings or bands, indicate areas of relatively higher temperature and areas of relatively lower temperature. It is contemplated that the particular thermally-sensitive medium 331 used may be selected so as to display only a single temperature of interest as opposed to a range of temperatures.

Additionally, the imaging system 918 may record and store the settings and/or parameters of the electrosurgical power generating source 916 (e.g., temperature, impedance, power, current, voltage, mode of operation, duration of application of electromagnetic energy, etc.) associated with the creation of the image on the thermally-sensitive medium 331.

Following the acquisition of images created on the thermally-sensitive medium 331, the power generating source 916 may be deactivated and the energy applicator 1 withdrawn from the housing 302. The used thermally-sensitive medium 331 may be removed from the housing 302 and replaced with a new or un-used thermally-sensitive medium 331. The above-described method may be repeated for the same or different set of settings and/or parameters for the power generating source 916 and/or the same or different energy applicator 1 configuration.

Thermal profiling system 900 may be used in conjunction with any suitable hypothermic and/or ablative energy system including, for example, microwave energy systems employing microwave antennas for delivering ablative energy. The above-described thermal profiling system 900 has been specifically described in relation to the characterization of a single energy applicator 1. However, it is envisioned and within the scope of the present disclosure that test fixture assembly 300 be configured to receive multiple energy applicators, e.g., two or more, and for images and/or data to be acquired thereof, in accordance with the method described above.

During use of the thermal profiling system 900, the image acquisition unit 912 of the imaging system 918 acquires a series of images of the thermally-sensitive medium 331 with color bands formed thereon disposed around the energy applicator 1. Image acquisition unit 912 may acquire a series of images with varying time delays before image acquisition. In some embodiments, the image acquisition unit 912 acquires a time series of images wherein the series of images is recorded along time at uniform time intervals.

FIGS. 10, 12 and 14 show an energy applicator 1 disposed within the cut-out portion 332 of the thermally-sensitive medium 331 with schematically-illustrated representations of thermal radiation patterns "$S_1$", "$S_2$" and "$S_3$" respectively, formed on the thermally-sensitive medium 331 during use of the thermal profiling system 900 at time t equal to $t_1$, $t_2$ and $t_3$, respectively. In FIGS. 10, 12 and 14, a plurality of color bands (also referred to herein as temperature bands) are shown around the energy applicator 1. The shape, size and number of temperature bands on the thermally-sensitive medium 331 may be varied from the configurations depicted in FIGS. 10, 12 and 14.

Imaging system 918, according to various embodiments, includes an image processing unit 954 in communication with the image acquisition unit 912. A time series of image data acquired by the image acquisition unit 912 (or image data from other imaging modalities such as MRI) may be inputted and stored in a memory (not shown) of the image processing unit 954. According to embodiments of the present disclosure, one or more temperature bands (e.g., "$B_1$", "$B_2$", "$B_3$" and/or "$B_4$" shown in FIG. 14) may be selected, either manually by the user, e.g., using a pointing device (e.g., 27 shown in FIG. 1) and/or the touchscreen capability of a display device (e.g., 21 shown in FIG. 1), or automatically, e.g., by the image processing unit 954, for image processing to generate data for use in characterizing the energy applicator 1.

A method according to embodiments of the present disclosure includes thresholding to segment an image data by setting all pixels whose intensity values are above a predetermined threshold to a foreground value and all the remaining pixels to a background value.

FIGS. 11, 13 and 15 show thresholded pattern images "$T_1$", "$T_2$" and "$T_3$", respectively, of a portion of the thermally-sensitive medium of FIGS. 10, 12 and 14 showing a selected temperature band "$B_2$" at time t equal to $t_1$, $t_2$ and $t_3$, respectively.

Figure 16A:
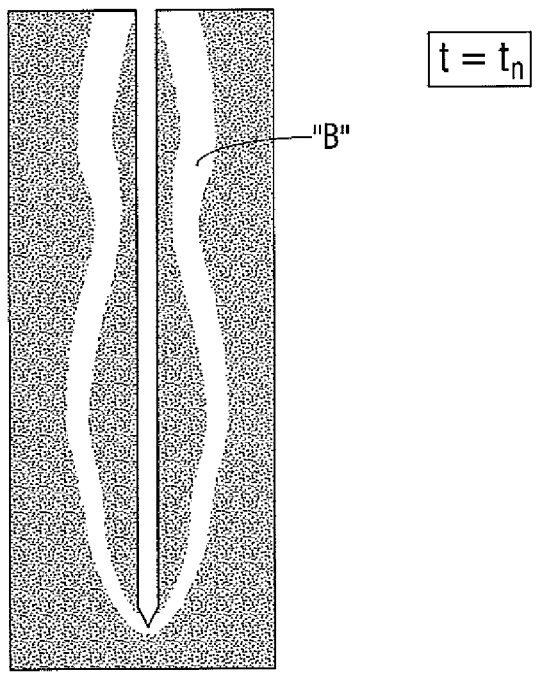
FIG. 16A is a schematic diagram illustrating a thresholded pattern image of a thermally-sensitive medium according to an embodiment of the present disclosure showing a selected temperature band at time t equal to $t_n$.
Figure 16B:
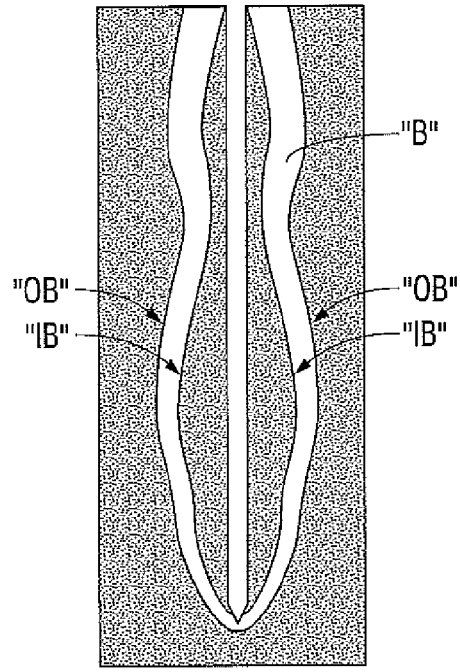
FIG. 16B is a schematic view of the thresholded pattern image of FIG. 16A shown with contour lines at the inner and outer boundaries of the temperature band.
Figure 17A:
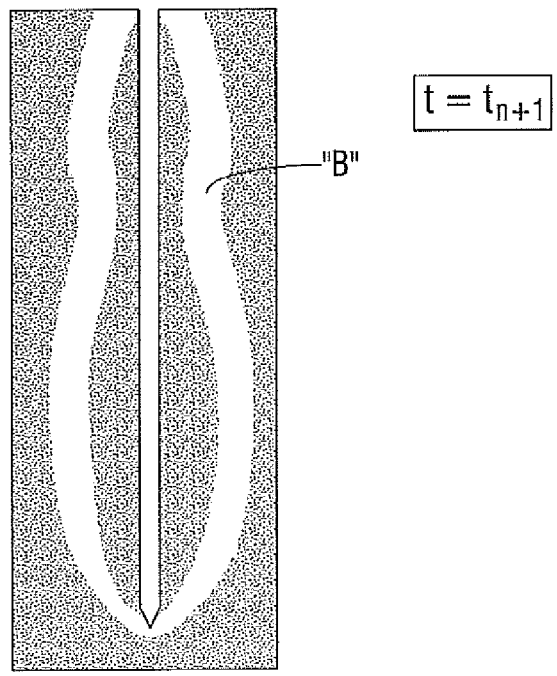
FIG. 17A is a schematic diagram illustrating a thresholded pattern image of a thermally-sensitive medium according to an embodiment of the present disclosure showing a selected temperature band at time t equal to $t_{n+1}$.
Figure 17B:
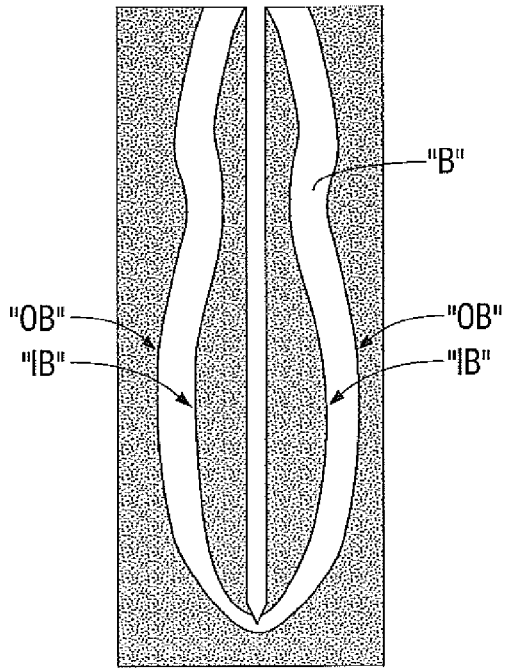
FIG. 17B is a schematic view of the thresholded pattern image of FIG. 17A shown with contour lines connecting a set of points at the inner and outer boundaries of the temperature band.

A method according to embodiments of the present disclosure includes generating image data on the basis of thresholded pattern images of the selected temperature band (e.g., "B" shown in FIGS. 16A and 17A) surrounded by an inner boundary (e.g., "IB" shown in FIGS. 16B and 17B) and/or an outer boundary (e.g., "OB" shown in FIGS. 16B and 17B).

FIG. 16A shows a selected temperature band "B" at time t equal to $t_n$, and FIG. 17B shows the temperature band "B" at time t equal to $t_{n+1}$. As illustratively shown in FIGS. 16B and 17B, thresholding of time-series image data may be used to detect an inner boundary and an outer boundary of the selected color band in each image data of the time-series image data.

Figure 19:
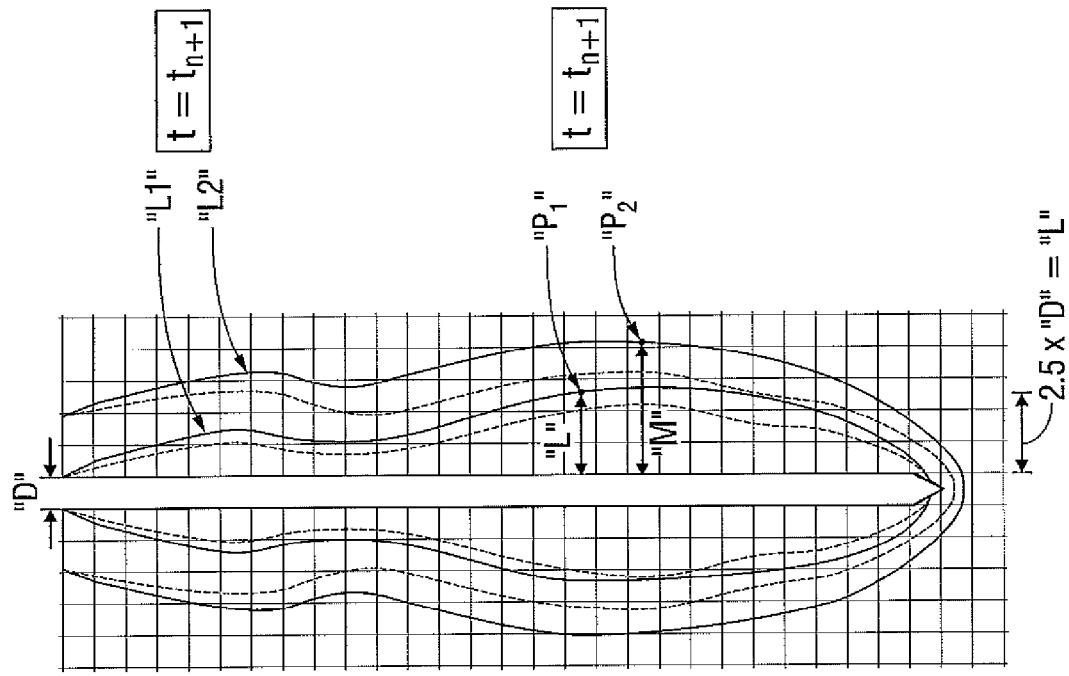
FIGS. 18 and 19 are schematic diagrams illustrating the positional relationship between points lying on the boundary lines of the temperature band of FIGS. 16B and 17B according to an embodiment of the present disclosure.
Figure 18:
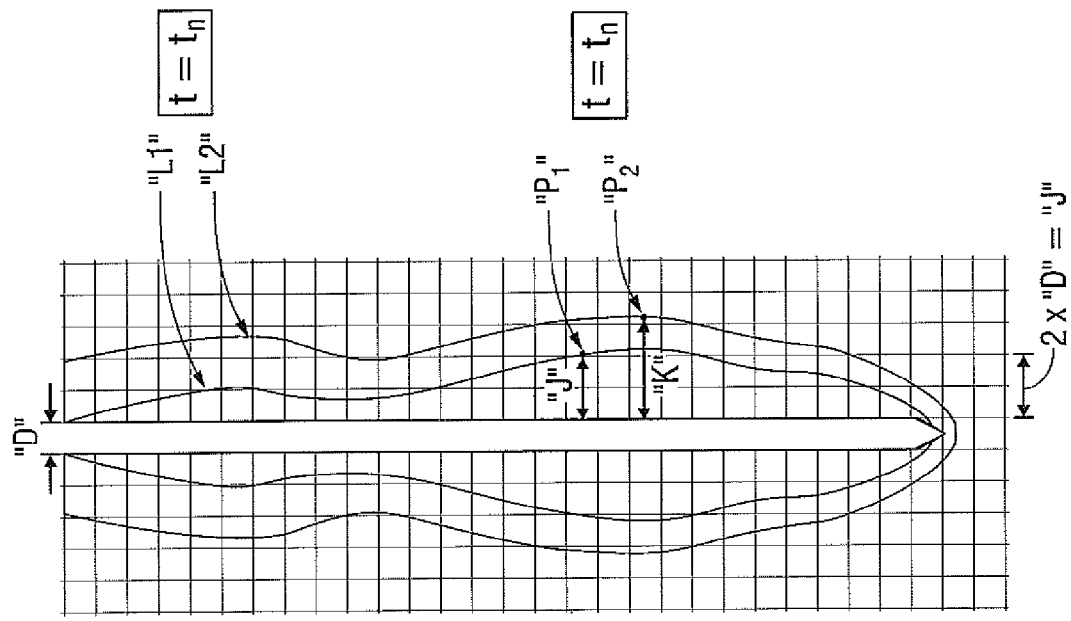

An example of the positional relationships between two points lying on the boundaries of a temperature band (e.g., "B" of FIGS. 16B and 17B) is shown in FIGS. 18 and 19. For illustrative purposes, the inner and outer boundaries "L1" and "L2", respectively, of a temperature band, at time t equal to $t_n$ (shown by the solid curved lines in FIG. 18 and the dashed curved lines in FIG. 19), and at time t equal to $t_{n+1}$ (shown by the solid curved lines in FIG. 19), are plotted on a coordinate grid having equal scale units "D". In the interest of simplicity, unit "D" may be taken to be equal to the width of the cut-out portion, for illustrative purposes. It is contemplated that other spatial data or features may be used to establish a measurement scale, such as grid lines or marks, or objects, placed on the thermally-sensitive medium prior to image acquisition, or the diameter of the energy applicator.

In FIGS. 18 and 19, each of the points "$P_1$" and "$P_2$" may correspond to a single pixel or to a group of pixels. Referring to FIG. 18, at time t equal to $t_n$, the point "$P_1$" on the inner boundary "L1" is spaced apart a length "J" from an edge point of the cut-out portion, and the point "$P_2$" on the outer boundary "L2" is spaced apart a length "K" from an edge point of the cut-out portion. In this example, the length "J" is equal to 2 times the unit "D". Turning now to FIG. 19, at time t equal to $t_{n+1}$, the point "$P_1$" on the inner boundary "L1" is spaced apart a length "L" from a cut-out portion edge point, and the point "$P_2$" on the outer boundary "L2" is spaced apart a length "M" from a cut-out portion edge point. In this example, the length "L" is equal to 2.5 times the unit "D". In the present example, it can be calculated from the coordinate grid that, from a time t equal to $t_n$ to t equal to $t_{n+1}$, the point "$P_1$" on the inner boundary "L1" of the temperature band moves, from a first position to a second position on the coordinate grid, a distance equal to one-half of the unit "D". According to an embodiment of the present disclosure, determination of the positional change of point "$P_1$" on the inner boundary "L1" of the temperature band provides the value of the temperature difference, $\Delta T$, for use in calculating the specific absorption rate. The difference in time from a time t equal to $t_n$ to t equal to $t_{n+1}$ may be set by the frame rate of the image acquisition device (e.g., 912 shown in FIG. 9).

The specific absorption rate (SAR) may be calculated by the following equation:

$$SAR = c_\rho \frac{\Delta T}{\Delta t}, \quad (4)$$

where $c_\rho$ is the specific heat of the hydrogel 304 (in units of Joules/kg-° C.), $\Delta T$ is the temperature difference (° C.), and $\Delta t$ is the time period in accordance with the frame rate, or a fraction or multiple thereof, in seconds.

Hereinafter, a method of predicting a radiation pattern emitted by an energy applicator is described with reference to FIG. 22, and a method of analyzing time-series image data to determine the specific absorption rate around an energy applicator is described with reference to FIG. 23. It is to be understood that the steps of the methods provided herein may be performed in combination and in a different order than presented herein without departing from the scope of the disclosure.

Figure 22:
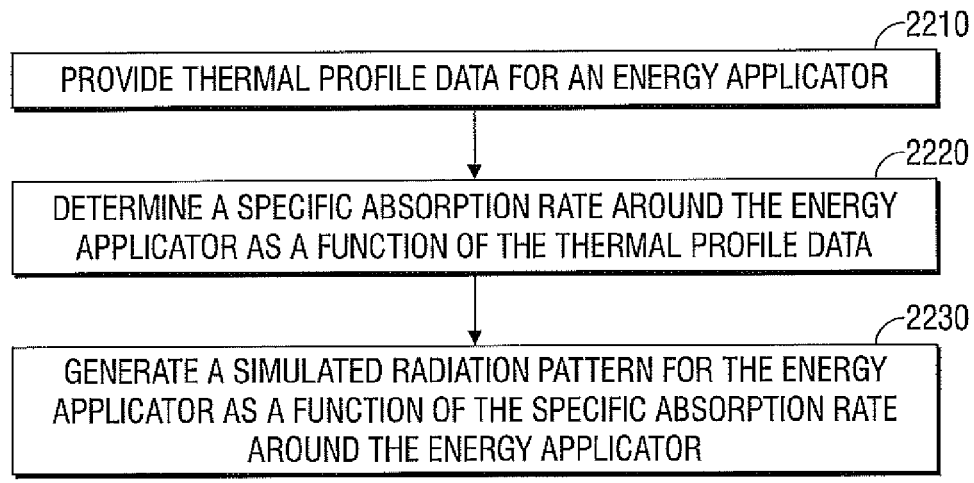
FIG. 22 is a flowchart illustrating a method of predicting a radiation pattern emitted by an energy applicator according to an embodiment of the present disclosure.

FIG. 22 is a flowchart illustrating a method of predicting a radiation pattern emitted by an energy applicator according to an embodiment of the present disclosure. In step 2210, thermal profile data (e.g., $202\text{-}202_n$ shown in FIG. 1) for an energy applicator (e.g., 1 shown in FIGS. 4 and 9) is provided. Providing thermal profile data for the energy applicator may include retrieving thermal profile data from a picture archiving and communication system (PACS) (e.g., 58 shown in FIG. 1) or a library (e.g., 200 shown in FIG. 1). Providing thermal profile data for the energy applicator, in step 2210, may include retrieving thermal profile data from an imaging system (e.g., 918 shown in FIG. 9).

In step 2220, a specific absorption rate around the energy applicator as a function of the thermal profile data is determined. Determining the specific absorption rate around the energy applicator as a function of the thermal profile data, in step 2220, may include selecting a color band of the thermal profile data. One or more color bands (e.g., "$B_1$", "$B_2$", "$B_3$" and/or "$B_4$" shown in FIG. 14) may be selected. In embodiments, the thermal profile data may be displayed on a display device (e.g., 21 shown in FIG. 9). The display device may include touchscreen capability, which may allow user selection of the color band(s), e.g., by contacting the display panel with a stylus or fingertip. A pointing device (e.g., 27 shown in FIG. 1), may be provided to enable user selection of the color band(s). Color band(s) may additionally, or alternatively, be selected automatically, e.g., by an image processing unit (e.g., 954 shown in FIG. 9).

Determining the specific absorption rate around the energy applicator as a function of the thermal profile data, in step 2220, may include thresholding a plurality of image data of the thermal profile data to detect at least one boundary of the selected color band in each image data of the plurality of image data. In some embodiments, determining the specific absorption rate around the energy applicator as a function of the thermal profile data may include the steps of determining a change in temperature as a function of positional transition of at least one boundary of the selected color band in each image data of the plurality of image data, and calculating a specific absorption rate around the energy applicator as a function of the determined change in temperature. The specific absorption rate calculation may be performed using equation (4), as discussed hereinabove.

In step 2230, one or more simulated radiation patterns (e.g., "P1" and "P2" shown in FIGS. 20 and 21, respectively) are generated for the energy applicator as a function of the determined specific absorption rate (SAR). Simulated radiation patterns for an energy applicator as a function of the SAR around the energy applicator may be generated by any suitable method. For example, the Pennes' bio-heat equation coupled with electrical field equations in a finite element analysis (FEA) environment may be used to generate simulated radiation patterns for an energy applicator as a function of the SAR around the energy applicator. The simulated radiation pattern(s) may be displayed on a display device (e.g., 21 shown in FIG. 1), e.g., to facilitate planning of a procedure. For example, the simulated radiation pattern(s) may be used as a predictive display of how an ablation will occur prior to the process of ablating.

Figure 23:
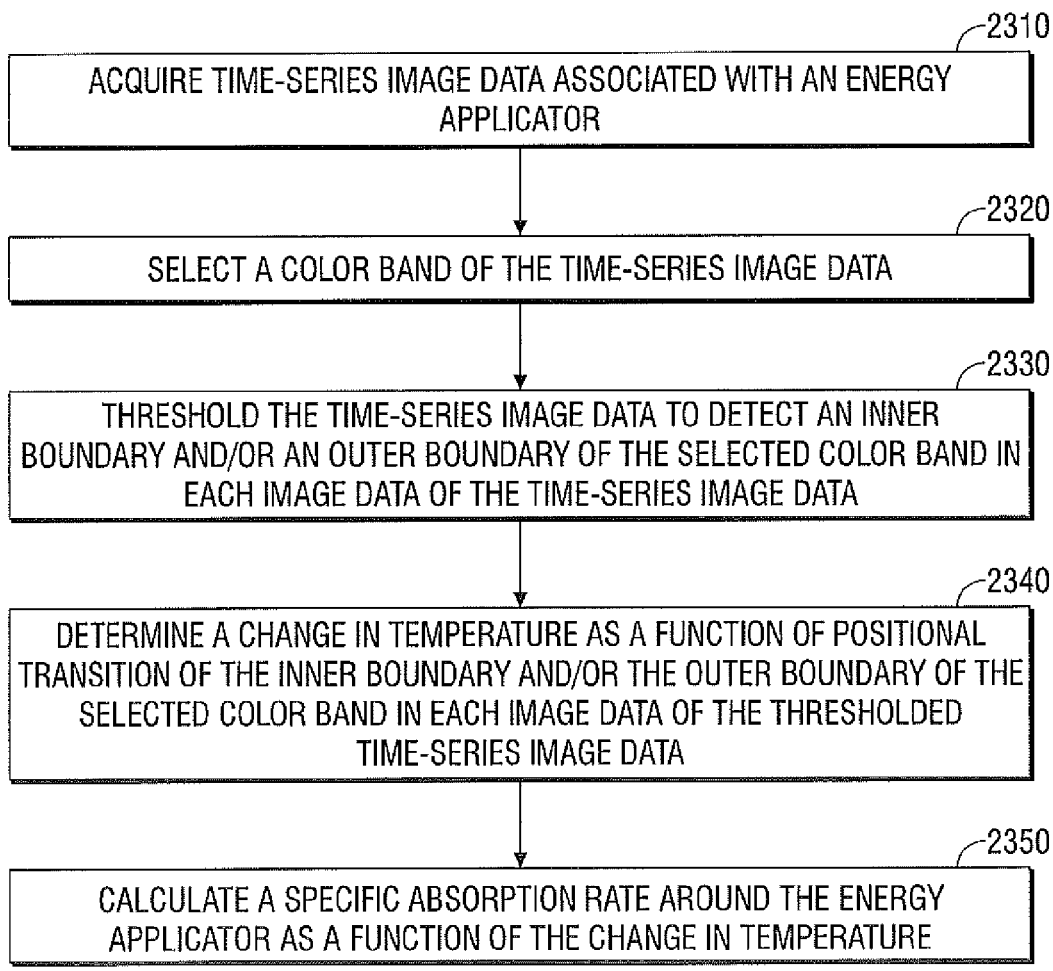
FIG. 23 is a flowchart illustrating a method of analyzing time-series image data to determine the specific absorption rate around an energy applicator according to an embodiment of the present disclosure.
Figure 24:
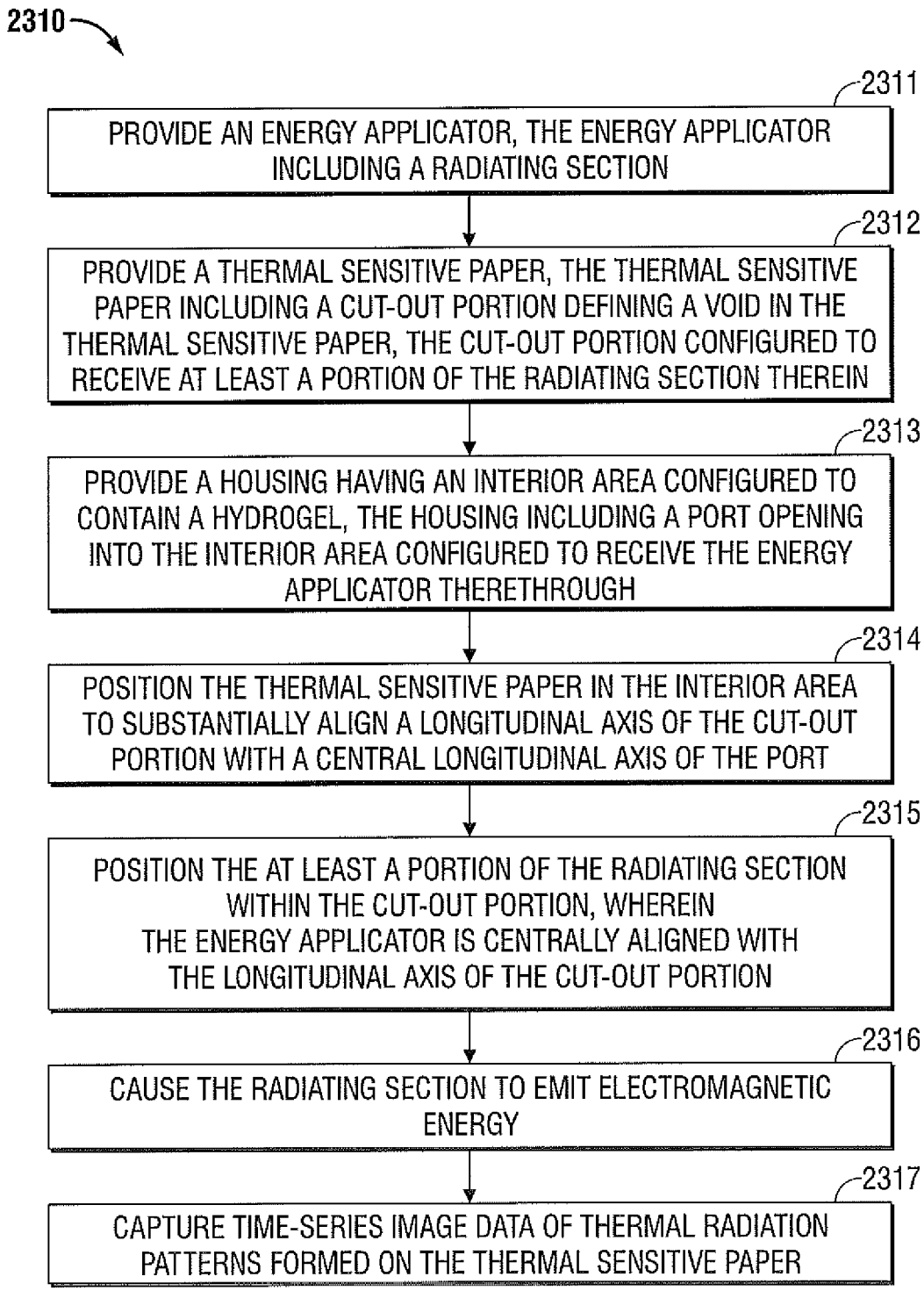
FIG. 24 is a flowchart illustrating a sequence of method steps for performing the step 2310 of the method illustrated in FIG. 23 according to an embodiment of the present disclosure.

FIG. 23 is a flowchart illustrating a method of analyzing time-series image data to determine the specific absorption rate around an energy applicator according to an embodiment of the present disclosure. In step 2310, time-series image data (e.g., "$S_1$", "$S_2$" and "$S_3$" shown in FIGS. 10, 12 and 14, respectively) associated with an energy applicator (e.g., 1 shown in FIGS. 4 and 9) is acquired. For example, an image acquisition unit (e.g., 912 shown in FIG. 9) including a device capable of generating input pixel data representative of an image may be used to capture time-series image data of thermal radiation patterns formed on a thermally-sensitive medium (e.g., 331 shown in FIG. 9) associated with the energy applicator. A housing (e.g., 302 shown in FIGS. 2 through 4) having an interior area (e.g., 301 shown in FIG. 2) configured to contain a hydrogel material (e.g., 304 shown in FIG. 9) therein, and including a port (e.g., 303 shown in FIG. 3) opening into the interior area and configured to receive the energy applicator therethrough may be provided for this purpose. As described in detail below, FIG. 24 is a flowchart illustrating a sequence of method steps for performing the step 2310 according to an embodiment of the present disclosure.

In step 2320, a color band (e.g., "$B_2$" shown in FIGS. 10, 12 and 14) of the time-series image data is selected. Selecting the color band of the time series image data, in step 2320, may include outputting one or more image data of the time-series image data to a display device. A pointing device may be provided to enable user selection of the color band. According to embodiments of the present disclosure, one or more temperature bands (e.g., "$B_1$", "$B_2$", "$B_3$" and/or "$B_4$" shown in FIG. 14) may be selected, either manually by the user, e.g., using a pointing device (e.g., 27 shown in FIG. 1) and/or the touchscreen capability of a display device (e.g., 21 shown in FIG. 1), or automatically, e.g., by an image processing unit (e.g., 954 shown in FIG. 9).

In step 2330, the time-series image data is thresholded (e.g., "$T_1$", "$T_2$" and "$T_3$" shown in FIGS. 11, 13 and 15, respectively) to detect an inner boundary (e.g., "IB" shown in FIGS. 16B and 17B) and/or an outer boundary (e.g., "OB" shown in FIGS. 16B and 17B) of the selected color band in each image data of the thresholded time-series image data.

Thresholding the time-series image data, in step 2330, may include setting all pixels whose intensity values are above a predetermined threshold to a foreground value and all the remaining pixels to a background value.

In step 2340, a change in temperature is determined as a function of positional transition (e.g., "$P_1$" from "J" to "L" shown in FIGS. 18 and 19) of the inner boundary (e.g., "L1" shown in FIGS. 18 and 19) and/or the outer boundary (e.g., "L2" shown in FIGS. 18 and 19) of the selected color band in each image data of the thresholded time-series image data.

In step 2350, a specific absorption rate around the energy applicator is calculated as a function of the determined change in temperature. Calculating the specific absorption rate, in step 2340, may include obtaining a frame rate of an image acquisition device associated with the time-series image data. The specific absorption rate calculation may be performed using equation (4), as discussed hereinabove.

FIG. 24 is a flowchart illustrating a sequence of method steps for performing the step 2310, acquiring time-series image data associated with an energy applicator, of the method illustrated in FIG. 23. In step 2311, an energy applicator (e.g., 1 shown in FIGS. 4 and 9) is provided, wherein the energy applicator includes a radiating section (e.g., "R1" shown in FIG. 4). In embodiments, the radiating section is electrically coupled via a transmission line (e.g., 91 shown in FIG. 9) to an electrosurgical power generating source (e.g., 916 shown in FIG. 9). The energy applicator may include a feedline (e.g., 1a shown in FIGS. 4 and 9) electrically coupled between the radiating section and the transmission line.

In step 2312, a thermally-sensitive medium (e.g., 331 shown in FIG. 5) including a cut-out portion (e.g., 332 shown in FIG. 5) defining a void in the thermally-sensitive medium is provided. The cut-out portion is configured to receive at least a portion of the radiating section of the energy applicator therein. The cut-out portion may be configured to provide a gap (e.g., "G" shown in FIG. 7) between the energy applicator and the thermally-sensitive medium at an edge of the cut-out portion. The thermally-sensitive medium may have a thermal sensitivity of about one degree Celsius.

In step 2313, a housing (e.g., 302 shown in FIGS. 2 through 4) having an interior area (e.g., 301 shown in FIG. 2) configured to contain a hydrogel material (e.g., 304 shown in FIG. 9) is provided. The housing includes a port (e.g., 303 shown in FIG. 3) opening into the interior area and configured to receive the energy applicator therethrough.

In step 2314, the thermally-sensitive medium is positioned in the interior area to substantially align a longitudinal axis (e.g., "A-A" shown in FIG. 5) of the cut-out portion with a central longitudinal axis (e.g., "A-A" shown in FIG. 3) of the port. To facilitate the positioning of the thermally-sensitive medium in the interior area, a support member (e.g., 325 shown in FIGS. 3 and 6) configured to support at least a portion of the thermally-sensitive medium may be provided. The support member may include a channel (e.g., 328a shown in FIG. 6) having a central longitudinal axis (e.g., "A-A" shown in FIG. 6) substantially aligned with the central longitudinal axis of the port.

Figure 8:
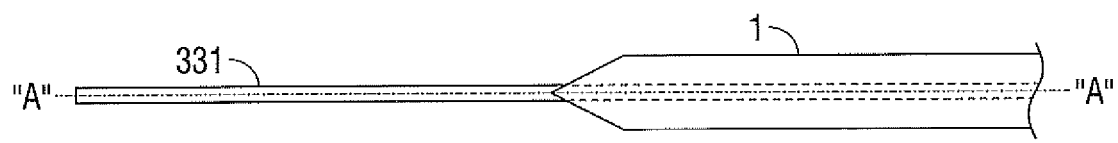

In step 2315, the radiating section (e.g., "R1" shown in FIG. 4), or portion thereof, of the energy applicator is positioned within the cut-out portion (e.g., 332 shown in FIG. 7), wherein the energy applicator is centrally aligned with the longitudinal axis of the cut-out portion, e.g., as shown in FIGS. 7 and 8.

In step 2316, the radiating section is caused to emit electromagnetic energy. In some embodiments, energy from the electrosurgical power generating source is transmitted via the transmission line to the radiating section, causing the radiating section to emit electromagnetic energy. Electromagnetic energy emitted by the radiating section causes thermal radiation patterns to be formed in the thermally-sensitive medium.

In step 2317, time-series image data of thermal radiation patterns formed on the thermally-sensitive medium (e.g., "$S_1$", "$S_2$" and "$S_3$" shown in FIGS. 10, 12 and 14, respectively) is captured. An image acquisition unit (e.g., 912 shown in FIG. 9) including a device capable of generating input pixel data representative of an image, e.g., a digital camera or digital video recorder, may be provided for this purpose. The image acquisition unit is configured to capture time-series image data of thermal radiation patterns formed on the thermally-sensitive medium, and may be disposed over the interior area of the housing or otherwise suitably positioned to facilitate image capture of the thermally-sensitive medium, or portion thereof.

The above-described systems and methods may involve the use of data associated with image analysis of a thermal phantom for calculation of SAR (e.g., used to predict a radiation pattern emitted by an energy applicator) to facilitate planning and effective execution of a procedure, e.g., an ablation procedure.

The above-described systems and methods may involve the use of image data including tissue temperature information to calculate SAR as a function of the tissue temperature information during a procedure (e.g., used to determine one or more operating parameters associated with an electrosurgical power generating source). As described above, image data including tissue temperature information (e.g., acquired by one or more imaging modalities) may be stored in DICOM format in a PACS database, and the stored image data may be retrieved from the PACS database prior to and/or during a procedure, e.g., for use in calculating SAR during the procedure. As described above, image data including tissue temperature information may be received from one or more imaging modalities during a procedure, e.g., for use in calculating SAR during the procedure. One or more operating parameters associated with an electrosurgical power generating source may be determined using real-time (or near real-time) tissue temperature data acquired from one or more imaging modalities during the procedure, e.g., an ablation procedure.

According to various embodiments of the present disclosure, the SAR around an energy application, as determined by the above-described methods, may be used to predict a radiation pattern emitted by an energy applicator, and/or control the positioning of an electrosurgical device (e.g., rotation of a energy applicator with a directional radiation pattern to avoid ablating sensitive structures, such as large vessels, healthy organs or vital membrane barriers), and/or control an electrosurgical power generating source operatively associated with an energy applicator.

Although embodiments have been described in detail with reference to the accompanying drawings for the purpose of illustration and description, it is to be understood that the inventive processes and apparatus are not to be construed as limited thereby. It will be apparent to those of ordinary skill in the art that various modifications to the foregoing embodiments may be made without departing from the scope of the disclosure.

What is claimed is:

1. A method of predicting a radiation pattern emitted by at least one energy applicator of a plurality of energy applicators, the method comprising:
    imaging a first target region during the application of energy thereto via the at least one energy applicator of the plurality of energy applicators;
    storing time-series of images along with a thermal profile for each of the plurality of energy applicators in a library;
    storing a plurality of parameters associated with each of the plurality of energy applicators in the library;
    calculating a specific absorption rate (SAR) of each energy applicator of the plurality of energy applicators from the images, the SAR calculated by factoring design of each of the plurality of energy applicators, ablation time, wattage of the ablation energy, and tumor size and location;
    selecting one of the plurality of energy applicators;
    imaging a second target region for which a radiation pattern prediction is desired;
    providing the thermal profile for the selected energy applicator; and
    generating a simulated radiation pattern for the selected energy applicator as a function of the calculated SAR around the selected energy applicator.

2. The method of claim 1, further comprising displaying the simulated radiation pattern on a display device to facilitate planning of a procedure.

3. The method of claim 1, wherein providing the thermal profile for the selected energy applicator includes retrieving thermal profiles from a picture archiving and communication system (PACS).

4. The method of claim 1, wherein providing the thermal profile for the selected energy applicator includes retrieving thermal profiles from an imaging system.

5. The method of claim 1, further comprising using the thermal profile of the selected energy applicator as feedback to enable continuous adjustment of the position and orientation of the selected energy applicator.

6. The method of claim 1, further comprising relating the plurality of parameters to at least energy applicator dimensions, an ablation length, an ablation diameter, and ablation pattern topology.

7. The method of claim 1, further comprising thresholding a plurality of images to detect at least one boundary of a temperature band selected in each image data of the plurality of images.

8. The method of claim 7, further comprising determining a change in temperature as a function of positional transition of the at least one boundary of the selected temperature band in each image of the plurality of images.

9. A method of analyzing time-series of image data to calculate a specific absorption rate (SAR) around at least one energy applicator of a plurality of energy applicators, the method comprising:
    acquiring a time-series of image data associated with the at least one energy applicator of the plurality of energy applicators;
    storing the time-series of image data along with a thermal profile for each of the plurality of energy applicators in a library;
    storing a plurality of parameters associated with each of the plurality of energy applicators in the library;
    selecting a color band of the time-series of image data of the at least one energy applicator;
    thresholding the time-series of image data of the at least one energy applicator to detect an inner boundary and an outer boundary of the selected color band in each image data of the thresholded time-series of image data of the at least one energy applicator;
    determining a change in temperature as a function of positional transition of one of the inner boundary or the outer boundary of each image data of the thresholded time-series of image data of the at least one energy applicator;

calculating the SAR by factoring design of each of the plurality of energy applicators, ablation time, wattage of the ablation energy, and tumor size and location; and generating a simulated radiation pattern for the at least one energy applicator as a function of the calculated SAR around the at least one energy applicator.

10. The method of claim 9, wherein acquiring the time-series of image data associated with the at least one energy applicator includes:

energizing the at least one energy applicator; and capturing time-series image of data of thermal radiation patterns formed on a thermally-sensitive medium associated with the at least one energy applicator.

11. The method of claim 10, wherein capturing the time-series of image data of thermal radiation patterns formed on the thermally-sensitive medium associated with the at least one energy applicator includes delivering electromagnetic energy to a radiating section of the at least one energy applicator.

12. The method of claim 10, further comprising providing the thermally-sensitive medium with a cut-out portion defining a void in the thermally-sensitive medium, the cut-out portion matching an outer profile of the energy applicator.

13. The method of claim 12, wherein the cut-out portion receives at least a portion of a radiating section of the at least one energy applicator.

14. The method of claim 13, wherein the cut-out portion provides a gap between the at least a portion of a radiating section and the thermally-sensitive medium at an edge of the cut-out portion.

15. The method of claim 9, wherein selecting the color band of the time series of image data includes outputting at least one image data of the time-series of image data to a display device.

16. The method of claim 9, further comprising relating the plurality of parameters to at least energy applicator dimensions, an ablation length, an ablation diameter, and ablation pattern topology.

* * * * *